United States Patent
Perry et al.

(10) Patent No.: US 7,641,668 B2
(45) Date of Patent: Jan. 5, 2010

(54) FLUID DELIVERY SYSTEM AND RELATED METHODS OF USE

(75) Inventors: Stephen J. Perry, Shirley, MA (US);
Michele B. Carter, Ashland, MA (US);
David R. Conti, Stoneham, MA (US);
Thomas F. Janecek, Flagstaff, AZ (US);
Bryan D. Knodel, Flagstaff, AZ (US);
Anthony Scott Hollars, Tucson, AZ (US); Peter Crowley, Norfolk, MA (US); Donald C. Hovey, Sherborn, MA (US); William Lucas Churchill, Boston, MA (US); John C. Golden, Norton, MA (US); Yem Chin, Burlington, MA (US); Mark L. Adams, Stoughton, MA (US); Carleton E. Yee, San Diego, CA (US); Otto E. Anderhub, Miami, FL (US)

(73) Assignee: SCIMED Life Systems, Inc., Maple Grove, MN (US)

( * ) Notice: Subject to any disclaimer, the term of this patent is extended or adjusted under 35 U.S.C. 154(b) by 1330 days.

(21) Appl. No.: 10/439,334

(22) Filed: May 16, 2003

(65) Prior Publication Data

US 2004/0230157 A1    Nov. 18, 2004

(51) Int. Cl.
*A61M 29/00* (2006.01)
*A61F 2/06* (2006.01)
(52) U.S. Cl. .................... 606/192; 604/99.01
(58) Field of Classification Search ............ 606/191, 606/192, 194, 198; 604/96.01, 97.03, 99.01, 604/99.02, 99.03, 100.03
See application file for complete search history.

(56) References Cited

U.S. PATENT DOCUMENTS

| 274,470 A | 3/1883 | Detterer |
| 966,861 A | 8/1910 | Rubly |
| 1,457,988 A | 6/1923 | Miller |
| 3,905,366 A | 9/1975 | Callahan et al. |
| 4,231,715 A | 11/1980 | Gleichner |
| 4,312,343 A | 1/1982 | LeVeen et al. |
| 4,322,022 A | 3/1982 | Bergman |
| 4,322,254 A | 3/1982 | Van Til et al. |
| 4,367,739 A | 1/1983 | LeVeen et al. |

(Continued)

FOREIGN PATENT DOCUMENTS

EP    0 075 735 A1    4/1983

(Continued)

OTHER PUBLICATIONS

International Search Report dated Sep. 28, 2004.

*Primary Examiner*—Vy Q Bui
(74) *Attorney, Agent, or Firm*—Finnegan, Henderson, Farabow, Garrett & Dunner, L.L.P.

(57) ABSTRACT

An apparatus and method for ejecting fluid from a fluid delivery system. The fluid delivery system has a pneumatic assembly that when triggered injects gas into a hydraulic assembly, which in turn ejects fluid through an external interface. An electronic interface displays various measurements, for example, how much fluid has been ejected and if the hydraulic system is closed the pressure of the system. The pneumatic assembly can also be depressurized such that fluid can reenter the hydraulic assembly through the external interface.

46 Claims, 16 Drawing Sheets

U.S. PATENT DOCUMENTS

| | | | |
|---|---|---|---|
| 4,370,982 A | 2/1983 | Reilly | |
| 4,429,724 A | 2/1984 | Dorros et al. | |
| 4,439,185 A | 3/1984 | Lundquist | |
| 4,439,186 A | 3/1984 | Kuhl | |
| 4,452,267 A | 6/1984 | Ott et al. | |
| 4,476,866 A | 10/1984 | Chin | |
| 4,565,209 A | 1/1986 | Ruchser et al. | |
| 4,583,974 A | 4/1986 | Kokernak | |
| 4,632,669 A | 12/1986 | Phipps, Sr. et al. | |
| 4,651,738 A | 3/1987 | Demer et al. | |
| 4,654,027 A | 3/1987 | Dragan et al. | |
| 4,655,749 A | 4/1987 | Fischione | |
| 4,710,179 A | 12/1987 | Haber et al. | |
| 4,723,938 A | 2/1988 | Goodin et al. | |
| 4,740,203 A | 4/1988 | Hoskins et al. | |
| 4,743,230 A | 5/1988 | Nordquest | |
| 4,758,223 A | 7/1988 | Rydell | |
| 4,781,192 A | 11/1988 | Demer | |
| 4,790,821 A | 12/1988 | Stines | |
| 4,808,165 A | 2/1989 | Carr | |
| 4,810,249 A | 3/1989 | Haber et al. | |
| 4,832,692 A | 5/1989 | Box et al. | |
| 4,838,864 A | 6/1989 | Peterson | |
| 4,861,340 A | 8/1989 | Smith et al. | |
| 4,872,483 A | 10/1989 | Shah | |
| 4,902,278 A | 2/1990 | Maget et al. | |
| 4,919,121 A | 4/1990 | Rydell et al. | |
| 4,921,402 A | 5/1990 | Nelson et al. | |
| 4,929,238 A | 5/1990 | Baum | |
| 4,940,459 A | 7/1990 | Noce | |
| 4,944,726 A | 7/1990 | Hilal et al. | |
| 4,951,677 A | 8/1990 | Crowley et al. | |
| 4,976,725 A | 12/1990 | Chin et al. | |
| 5,004,472 A | 4/1991 | Wallace | |
| 5,005,754 A | 4/1991 | Van Overloop | |
| 5,009,662 A | 4/1991 | Wallace et al. | |
| 5,015,233 A | 5/1991 | McGough et al. | |
| 5,019,037 A | 5/1991 | Wang et al. | |
| 5,019,041 A | 5/1991 | Robinson et al. | |
| 5,021,046 A | 6/1991 | Wallace | |
| 5,047,015 A | 9/1991 | Foote et al. | |
| 5,057,078 A | 10/1991 | Foote et al. | |
| 5,084,060 A | 1/1992 | Freund et al. | |
| 5,100,385 A | 3/1992 | Bromander | |
| 5,135,488 A | 8/1992 | Foote et al. | |
| 5,137,514 A | 8/1992 | Ryan | |
| 5,147,300 A | 9/1992 | Robinson et al. | |
| 5,152,776 A | 10/1992 | Pinchuk | |
| 5,168,757 A | 12/1992 | Rabenau et al. | |
| 5,201,753 A | 4/1993 | Lampropoulos et al. | |
| 5,209,731 A | 5/1993 | Sterman et al. | |
| 5,209,732 A | 5/1993 | Lampropoulos et al. | |
| 5,213,115 A | 5/1993 | Zytkovicz et al. | |
| 5,215,523 A | 6/1993 | Williams et al. | |
| 5,259,838 A | 11/1993 | Taylor et al. | |
| 5,273,537 A | 12/1993 | Haskvitz et al. | |
| 5,279,563 A | 1/1994 | Brucker et al. | |
| 5,282,790 A | 2/1994 | Clement | |
| 5,284,480 A | 2/1994 | Porter et al. | |
| 5,290,260 A | 3/1994 | Stines | |
| 5,300,027 A | 4/1994 | Foote et al. | |
| 5,300,035 A | 4/1994 | Clement | |
| 5,306,248 A | 4/1994 | Barrington | |
| 5,318,534 A | 6/1994 | Williams et al. | |
| 5,336,183 A | 8/1994 | Greelis et al. | |
| 5,338,296 A | 8/1994 | Dalessandro et al. | |
| 5,342,304 A | 8/1994 | Tacklind et al. | |
| 5,348,535 A | 9/1994 | Cucin | |
| 5,383,888 A | 1/1995 | Zvenyatsky et al. | |
| 5,385,549 A | 1/1995 | Lampropoulos et al. | |
| 5,387,194 A | 2/1995 | Williams et al. | |
| 5,421,338 A | 6/1995 | Crowley et al. | |
| 5,425,713 A | 6/1995 | Taylor et al. | |
| 5,429,606 A * | 7/1995 | Robinson et al. | 604/97.03 |
| 5,431,629 A | 7/1995 | Lampropoulos et al. | |
| 5,431,662 A | 7/1995 | Nicholas | |
| 5,433,707 A | 7/1995 | Call | |
| 5,449,344 A | 9/1995 | Taylor et al. | |
| 5,449,345 A | 9/1995 | Taylor et al. | |
| 5,453,091 A | 9/1995 | Taylor et al. | |
| 5,458,571 A | 10/1995 | Lampropoulos et al. | |
| 5,460,609 A | 10/1995 | O'Donnell | |
| 5,466,221 A | 11/1995 | Zadini et al. | |
| 5,472,424 A | 12/1995 | Lampropoulos et al. | |
| 5,507,727 A | 4/1996 | Crainich | |
| 5,556,389 A | 9/1996 | Liprie | |
| 5,562,692 A | 10/1996 | Bair | |
| 5,571,115 A | 11/1996 | Nicholas | |
| 5,578,048 A | 11/1996 | Pasqualucci et al. | |
| 5,607,441 A | 3/1997 | Sierocuk et al. | |
| 5,618,266 A | 4/1997 | Liprie | |
| 5,634,910 A | 6/1997 | Kanner et al. | |
| 5,643,198 A | 7/1997 | Cucin | |
| 5,647,847 A | 7/1997 | Lafontaine et al. | |
| 5,707,382 A | 1/1998 | Sierocuk et al. | |
| 5,711,302 A | 1/1998 | Lampropoulos et al. | |
| 5,735,815 A | 4/1998 | Bair | |
| 5,795,323 A | 8/1998 | Cucin | |
| 5,817,034 A | 10/1998 | Milliman et al. | |
| 5,827,324 A | 10/1998 | Cassell et al. | |
| 5,840,061 A | 11/1998 | Menne et al. | |
| 5,840,064 A | 11/1998 | Liprie | |
| 5,853,384 A | 12/1998 | Bair | |
| 5,902,315 A | 5/1999 | DuBois | |
| 5,906,621 A | 5/1999 | Secrest et al. | |
| 5,913,870 A | 6/1999 | DeFonzo et al. | |
| 5,922,004 A | 7/1999 | DuBois | |
| 5,931,850 A | 8/1999 | Zadini et al. | |
| 5,951,517 A | 9/1999 | Lampropoulos et al. | |
| 5,961,439 A | 10/1999 | Chernomorsky et al. | |
| 5,971,722 A | 10/1999 | Maget et al. | |
| 5,980,528 A | 11/1999 | Salys | |
| 5,989,263 A | 11/1999 | Shmulewitz | |
| 5,989,274 A | 11/1999 | Davison et al. | |
| 6,024,720 A | 2/2000 | Chandler et al. | |
| 6,139,523 A | 10/2000 | Taylor et al. | |
| 6,179,815 B1 | 1/2001 | Foote | |
| 6,183,444 B1 | 2/2001 | Glines et al. | |
| 6,193,695 B1 | 2/2001 | Rippstein, Jr. | |
| 6,213,957 B1 | 4/2001 | Milliman et al. | |
| 6,273,861 B1 | 8/2001 | Bates et al. | |
| 6,296,653 B1 | 10/2001 | Zadini et al. | |
| 6,309,375 B1 | 10/2001 | Glines et al. | |
| 6,346,107 B1 | 2/2002 | Cucin | |
| 6,387,109 B1 | 5/2002 | Davison et al. | |
| 6,394,977 B1 | 5/2002 | Taylor et al. | |
| 6,394,995 B1 | 5/2002 | Solar et al. | |
| 6,416,033 B1 | 7/2002 | McKell et al. | |
| 6,447,501 B1 | 9/2002 | Solar et al. | |
| 6,464,663 B1 | 10/2002 | Zinger | |
| 6,471,671 B1 | 10/2002 | Urick et al. | |
| 6,482,188 B1 | 11/2002 | Rogers et al. | |
| 6,533,757 B1 | 3/2003 | Lampropoulos et al. | |
| 6,534,002 B1 | 3/2003 | Lin et al. | |
| 2002/0030170 A1 | 3/2002 | McKell et al. | |
| 2003/0025095 A1 | 2/2003 | Sticht | |
| 2003/0078538 A1 | 4/2003 | Neale et al. | |

FOREIGN PATENT DOCUMENTS

| | | |
|---|---|---|
| EP | 0 515 332 A1 | 11/1992 |
| EP | 0 396 353 B1 | 3/1995 |
| WO | WO 90/11101 | 10/1990 |

* cited by examiner

FLUID DELIVERY SYSTEM AND RELATED METHODS OF USE

FIELD OF THE INVENTION

The present invention relates to an apparatus and method for delivering fluid. In a particular embodiment, the present invention relates to a self-contained, gas-powered, hydraulically-controlled inflation system that is hand-held. The system may be used, for example, in connection with a medical device, and is especially suitable for use in connection with balloon dilatation.

BACKGROUND OF THE INVENTION

Gastrointestinal strictures are abnormal narrowings that have formed in the gastrointestinal tract. Gastrointestinal strictures come in several forms, among them benign and malignant strictures in the esophageal, pyloric, and colonic regions of the gastrointestinal tract. These strictures are undesirable because they interfere with the normal ingestion and digestion of food through the gastrointestinal tract. Such abnormal ingestion/digestion is often accompanied by undesirable side effects, such as gastric ulcer pain, anorexia, nausea, vomiting, discomfort, and Hematemesis.

Gastrointestinal strictures form for a variety of reasons. For example, benign esophageal strictures may be the result of diseases such as peptic esophagitis or gastroesophageal reflux. They may also be the result of congenital conditions, such as the presence of membranous diaphragms or webs in the esophagus. Additionally, they may be the result of injury or scarring in the esophagus due to the ingestion of toxic substances. Malignant strictures, on the other hand, are more often the result of gastrointestinal cancer. For example, one specific type of gastrointestinal cancer called Barrett's esophagus is a result of chronic gastroesophageal reflux disease (stomach acid continually enters the esophagus), and sometimes causes the formation of malignant strictures in the lower portion of the esophagus.

There are presently two known endoscopic methods of treating gastrointestinal strictures. The first is through the use of one or more rigid dilatators. In this method, a rigid dilatator of a selected size is introduced into the gastrointestinal tract through either the oral or rectal orifice and advanced to the stricture location. Once the rigid dilatator is positioned at the stricture location, it is forced through the stricture. Through this application of radial and shearing forces via the rigid dilatator, the stricture tears and/or expands. This first rigid dilatator may then be removed and, if desired, a larger rigid dilatator may then be advanced into the gastrointestinal tract and forced through the stricture. This process may be repeated until the stricture has been sufficiently dilated or altogether eliminated.

One problem associated with this treatment method, however, is that the use of sheer force sometimes causes trauma to the sensitive tissue in the gastrointestinal tract. In addition, the size of a rigid dilator is limited by the cross-sectional area of the portions of the gastrointestinal tract leading up to the stricture. Thus, due to the dilatator's size limitation, it may not be possible to expand the stricture beyond a certain size that is short of that particular gastrointestinal tract portion's normal cross-sectional area.

Another known endoscopic method of treating gastrointestinal strictures is by the use of balloon dilators such as, for example, a wire-guided balloon dilators or a fixed wire balloon dilators. When using a wire-guided balloon dilator, a separate wire is advanced through the gastrointestinal tract to the stricture location. Then, a balloon dilator is advanced over the wire to the stricture location. A balloon at the distal end of the dilator is positioned within the stricture and inflated to a desired size. The inflation fluid is passed from a proximal end of the dilator through the dilator catheter to the balloon. A fixed-wire balloon dilator is similar to the wire-guided balloon dilator except that the balloon is fixed to the end of the wire. Thus, the entire balloon and wire assembly is advanced together through the gastrointestinal tract to the stricture location, where the balloon is then expanded by filling it with fluid.

To inflate the balloon of a balloon dilator, the user may attach a syringe-like device to the proximal end of the dilatation catheter, and then manually inject sufficient fluid into the balloon so that it reaches a desired size. Although such a system can be effective, it includes a number of steps to prepare the system, may require a certain level of manual dexterity and coordination between the user and assistants, and can lead to imprecise inflation of the balloon.

It is accordingly an object of the invention to create a fluid delivery system that is easy to use, precise, and effective.

SUMMARY OF THE INVENTION

In accordance with an aspect of the invention, an embodiment of the invention includes a balloon catheter having a proximal handle assembly. The balloon catheter may include a catheter attached to a handle assembly and configured to receive inflation fluid from the handle assembly, and a balloon attached to the distal end of the catheter and configured to receive inflation fluid from the catheter. The handle assembly of the balloon catheter may have a first assembly including an actuator connected to a reservoir for releasing pressurized fluid from the reservoir, and a second assembly having an inflation fluid chamber. The second assembly may be connected to the first assembly to receive pressurized fluid from the first assembly and connected to the catheter to deliver inflation fluid to the catheter in response to the receipt of pressurized fluid.

According to another aspect of the invention, an embodiment of the invention includes a fluid delivery system for connecting to a balloon catheter having a balloon. The fluid delivery system may include a first assembly having an actuator connected to a reservoir for releasing pressurized fluid from the reservoir, and a second assembly having an inflation fluid chamber. The second assembly may be connected to the first assembly to receive pressurized fluid from the first assembly and, in response to receipt of the pressurized fluid, deliver inflation fluid from the inflation fluid chamber to an external interface configured for connection to a balloon catheter. The fluid delivery system may also include an electronic interface to display information relating to a measurement of the fluid in the second assembly.

According to yet another aspect of the invention, an embodiment of the invention includes a fluid delivery system for connection to a balloon catheter having a balloon. The fluid delivery system may include a first means for providing pressurized fluid, a second means in fluid communication with the first means for receiving the pressurized fluid and, in response to receipt of the pressurized fluid, delivering inflation fluid to a balloon catheter. The fluid delivery system may also include a third means operably connected to the second means for measuring inflation fluid pressure in the second means and a fourth means for receiving an inflation fluid pressure measurement from the third means and displaying information relating to the inflation fluid pressure measurement.

According to still another aspect of the invention, an embodiment of the invention includes a method of delivering inflation fluid to a balloon of a balloon catheter. The method may include actuating an actuator to increase pressure, the increase in pressure forcing fluid to a balloon to increase a size of the balloon, measuring the pressure, deriving a balloon size from the measured pressure, and monitoring the balloon size on an electronic interface.

According to another aspect of the invention, an embodiment of the invention includes a method of dilating a stricture. The method may include advancing a balloon of a balloon catheter to a stricture location, actuating an actuator of a handle of the balloon catheter to increase a pressure in an inflation fluid chamber and force fluid to the balloon to increase a size of the balloon, measuring the pressure, electronically deriving the size of the balloon from the measured pressure, and monitoring the size of the balloon.

According to yet another aspect of the invention, an embodiment of the invention includes a method of dilating a stricture. The method may include advancing a balloon of a balloon catheter to a stricture location, actuating an actuator of a handle of the balloon catheter to increase a pressure in an inflation fluid chamber and force fluid to the balloon to increase a size of the balloon, measuring the pressure, and electronically displaying information based on the measured pressure.

According to still another aspect of the invention, an embodiment of the invention includes a fluid delivery system. The fluid delivery system may include an actuator connected to a valve for releasing a first pressurized fluid and an assembly defining a fluid chamber for containing a second fluid and having a volume that changes in response to the release of the first pressurized fluid. The fluid delivery system may also include an external interface in fluid communication with the fluid chamber, a sensor operably connected to the assembly to take measurements from the fluid chamber, and an electronic interface connected to the sensor to determine information relating to the measurements taken by the sensor.

According to another aspect of the invention, an embodiment of the invention includes a method of delivering fluid. The method may comprise releasing a pressurized fluid to decrease a volume of a chamber containing a delivery fluid, dispensing the delivery fluid from the chamber due to the decrease in volume of the chamber, taking measurements of at least one of pressurized fluid pressure, delivery fluid pressure, and the amount of delivery fluid dispensed, and displaying information relating to the measurements.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 4b is a schematic view of portions of the electronic interface of FIG. 4a.

FIG. 4c is a perspective view of inner portions of the electronic interface of FIG. 4a.

FIG. 4d-4e are schematic views of other inner portions of the electronic interface of FIG. 4a.

FIG. 5b is a perspective of a hydraulic stem of the hydraulic assembly of FIG. 5a.

FIG. 5d is a perspective view of a pressure sensor subassembly of the hydraulic assembly of FIG. 5a.

FIG. 5e is an end view of a primary piston of the hydraulic assembly of FIG. 5a.

FIGS. 5g-5i are front, side, and cross-sectional views respectively of the hydraulic cap of FIG. 5a.

FIG. 5j is a perspective view of an expansion piston of the hydraulic assembly of FIG. 5a.

FIGS. 5l-m are perspective views of a check valve of the hydraulic assembly of FIG. 5a.

FIG. 5n is a perspective view of a hydraulic cylinder of the hydraulic assembly of FIG. 5a.

FIG. 6b is a perspective view of a pneumatic valve of the pneumatic assembly of FIG. 6a.

FIG. 6e is a perspective view of a lever for use with the pneumatic assembly of FIG. 6a.

DESCRIPTION OF THE EMBODIMENTS

Reference will now be made in detail to the exemplary embodiments of the invention illustrated in the accompanying drawings. Wherever possible, the same reference numbers will be used throughout the drawings to refer to the same or like parts.

In the various embodiments, the invention pertains to a device for automatically delivering fluid. In the various embodiments and the specification, the use of the term "fluid" should be understood to include both liquid and gas. In the embodiments, a user may grip a handle portion of the device and trigger an actuator on the device which initiates fluid delivery from the device. Fluid delivery may be monitored through, for example, pressure measurements. The monitoring may be automatic, electronic, and/or displayed to the user. At a desired moment based, for example, on the pressure measurement, any other measured value, parameters based on a measured value, and/or comparisons to predetermined amounts, the device either manually or automatically stops the delivery of fluid. The user again may trigger the actuator on the device and have the fluid delivery portion of the process repeated, or the user may trigger a deflation portion and at least temporarily disable the device from being able to deliver fluid.

In some exemplary embodiments, the invention pertains to a device for automatically inflating a balloon dilator. In embodiments, a user may grip a handle portion of the device, trigger an actuator on the device which initiates fluid delivery to a balloon of a balloon dilator and inflates the balloon. The size of the balloon may be monitored through, for example, pressure measurements. The monitoring may be automatically performed by the device, preferably electronically, and displayed to the user. At a desired moment based, for example, on the pressure measurement, the balloon size, comparisons to predetermined pressures or sizes, or any other suitable parameter, the device either manually or automatically stops the delivery of fluid to the balloon. The user may leave the balloon inflated for a suitable amount of time, again trigger the actuator on the device to inflate the balloon further to another desired size, or trigger a deflation portion of the device to deflate the balloon.

Figure 1:
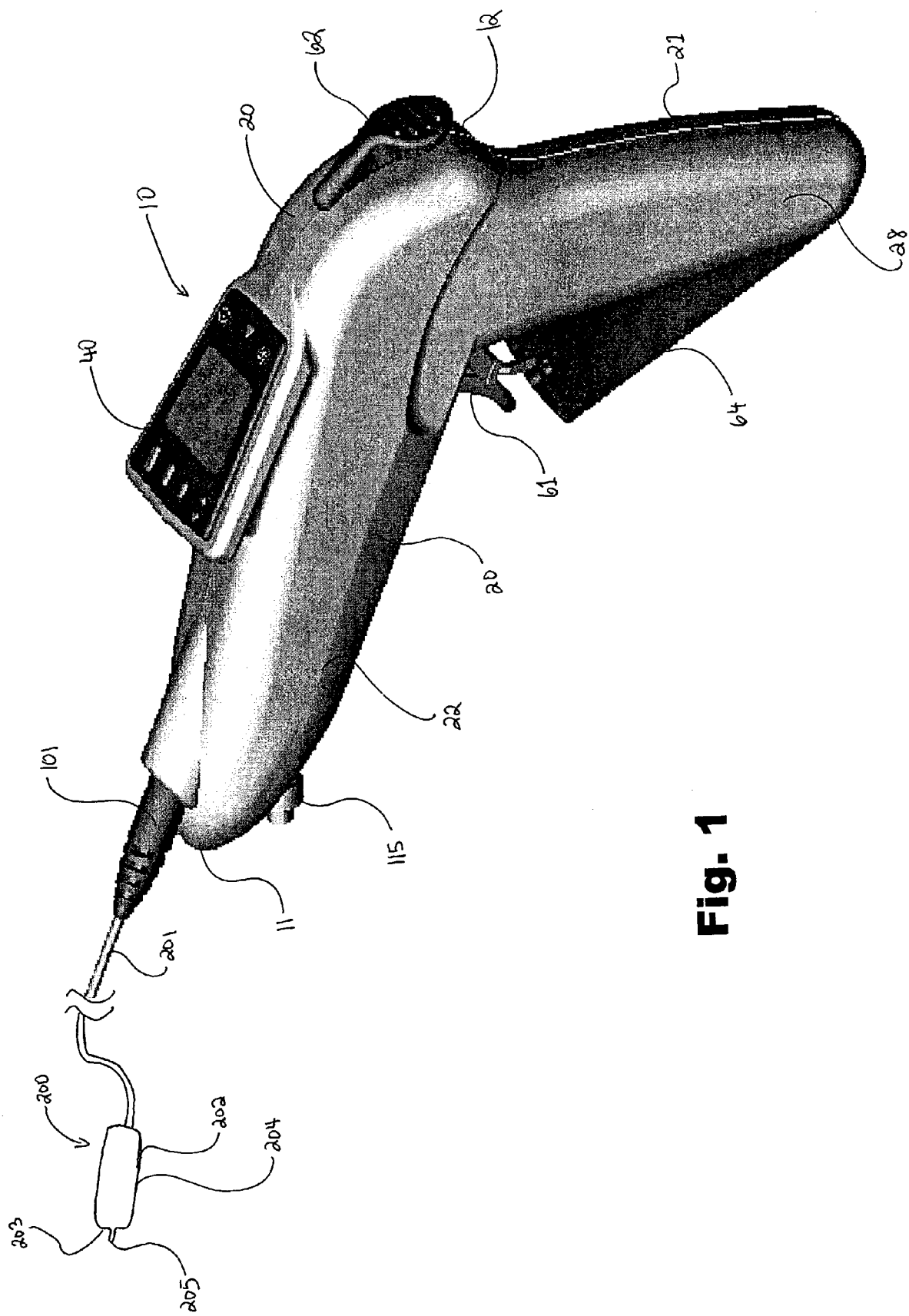
FIG. 1 is a perspective view of an integral fluid delivery system and balloon dilator, according to an embodiment of the present invention.
Figure 2:
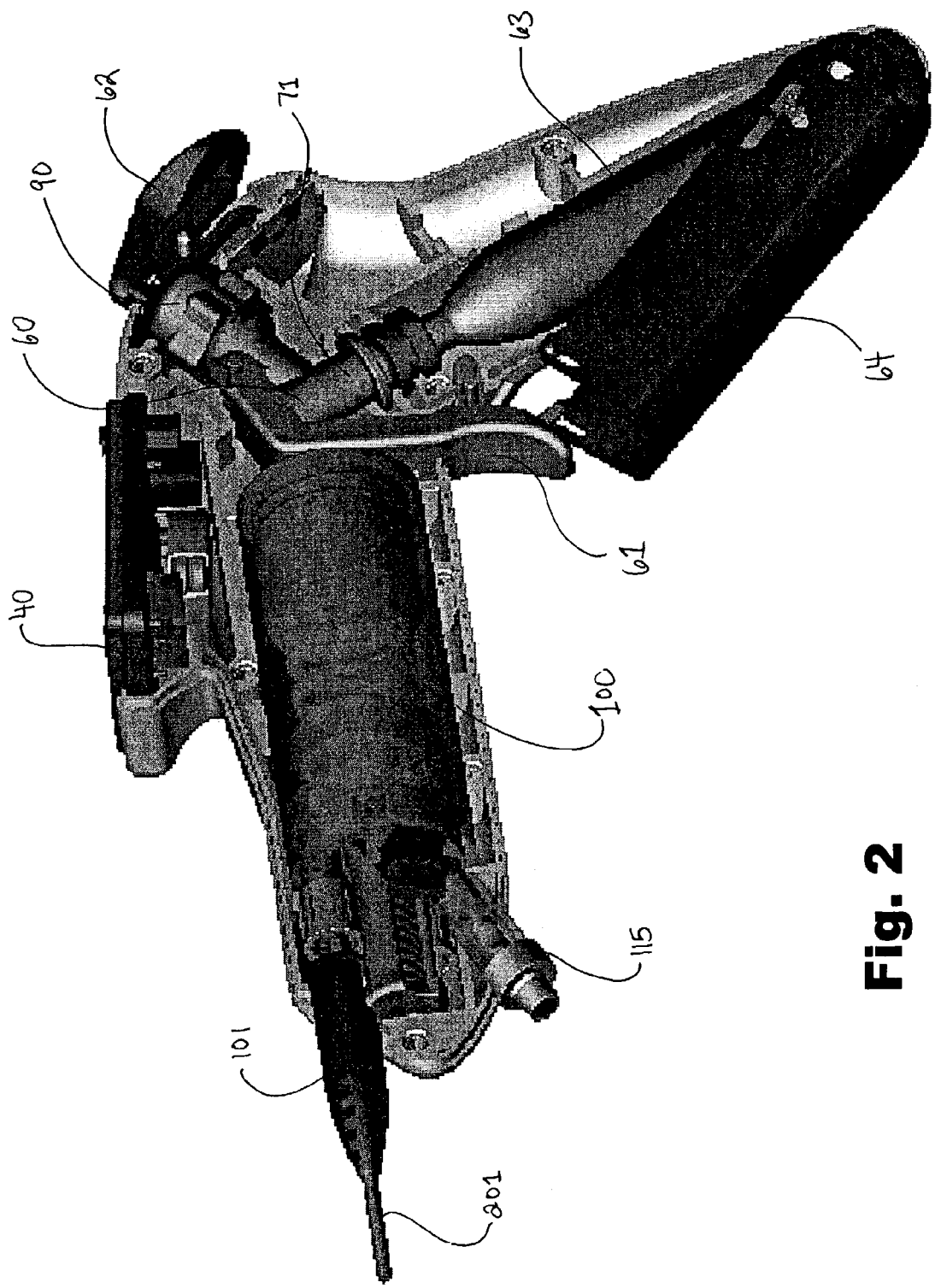
FIG. 2 is a perspective view of the inner portions of the fluid delivery system of FIG. 1.

FIGS. 1-2 show an exemplary embodiment of a fluid delivery system 10. As its main components, system 10 includes a housing 20 that contains an electronic interface 40, a hydraulic assembly 100, a pneumatic assembly 60, and an external interface 101. We will describe each such component in turn.

Figure 3A:
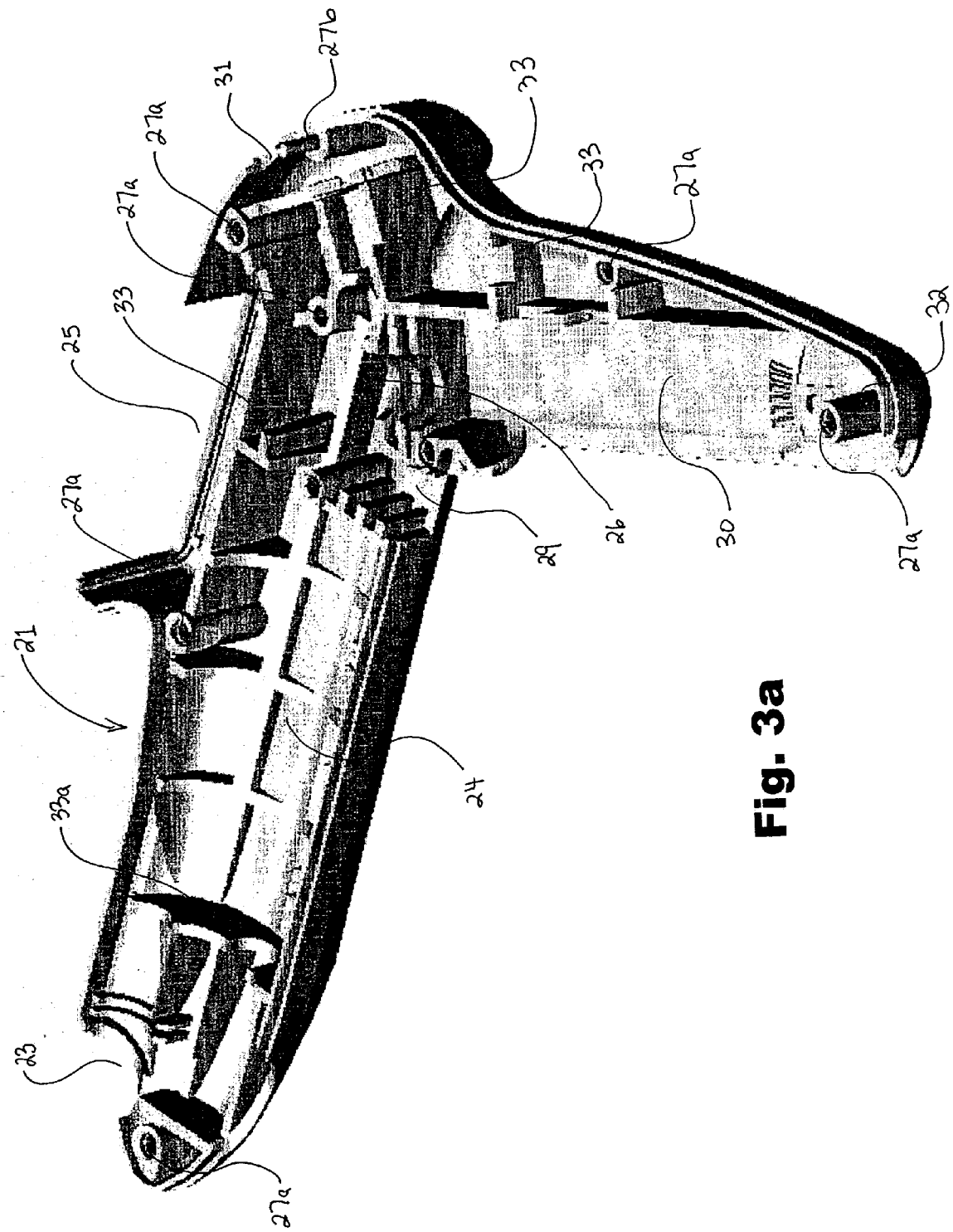
FIG. 3a is a perspective view of the inner portions of a right housing of the fluid delivery system of FIG. 1.
Figure 3B:
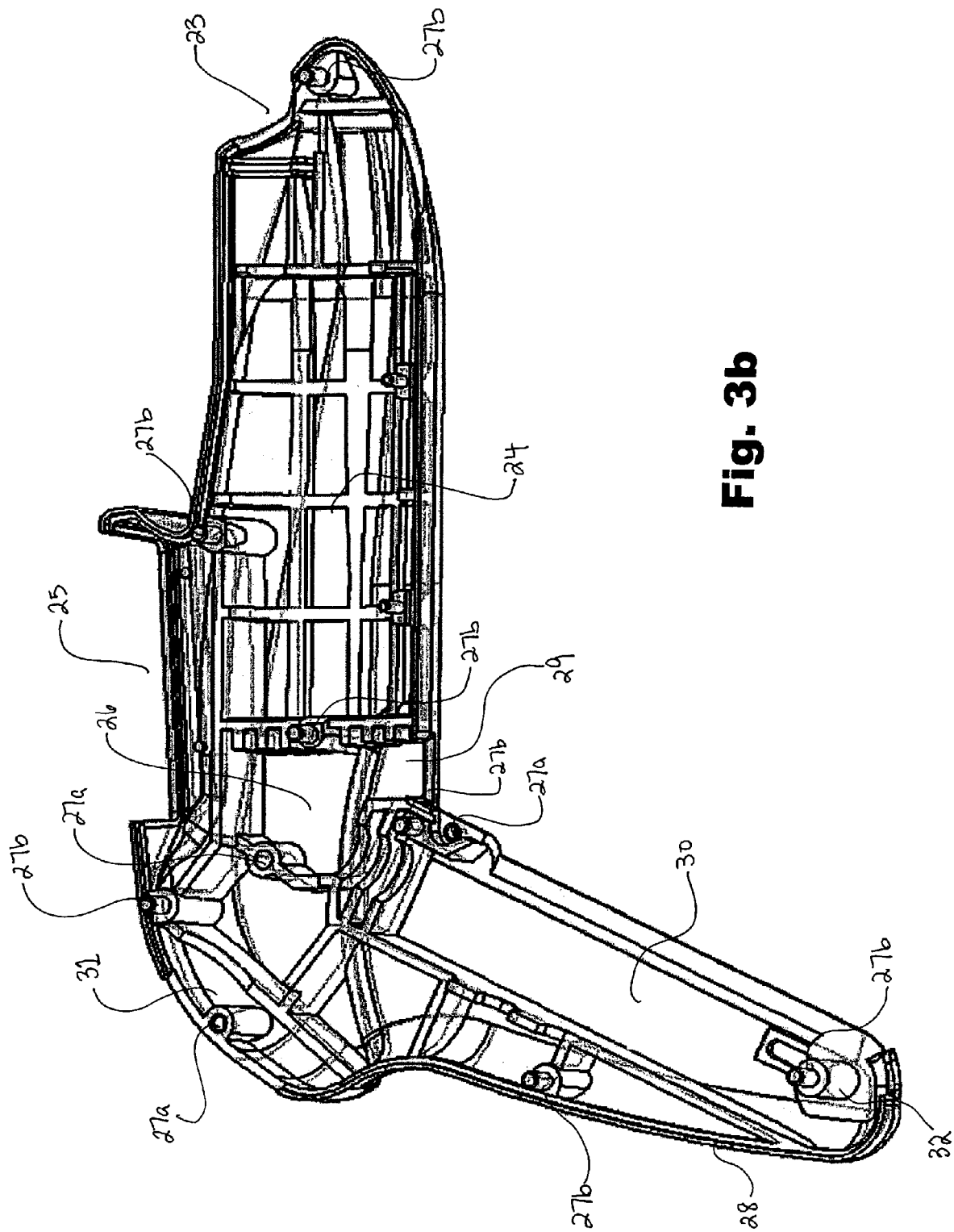
FIG. 3b is a schematic view of the inner portions of a left housing of the fluid delivery system of FIG. 1.

FIGS. 3a-3b show the interior of the housing 20 of an exemplary embodiment. The housing 20 may be comprised of a right housing portion 21, shown in FIG. 3a, that mates with and is connected to a left housing portion 22, shown in FIG. 3b.

Distributed about the interior of the housing portions 21, 22 may be a plurality of connectors. In this exemplary embodiment, the connectors include protruding connectors 27b and receiving connectors 27a. Thus, the right housing portion 21 may be mated to the left housing portion 22 by fitting the protruding connectors 27b on either housing portion 21, 22 into their corresponding receiving connectors on the opposite housing portion 21, 22. No particular arrangement of connectors 27 along the interior of the housing portions 21, 22 is necessary, however, a distribution of connectors 27 throughout the interior of the housing portions 21, 22 may facilitate a more solid mating of the housing portions 21, 22. In one exemplary embodiment, the connectors may be configured so that the protruding connectors 27b are press fit into their corresponding receiving connectors 27a so as to facilitate a more solid mating between the housing portions 21, 22.

The housing portions 21, 22 may have various areas for receiving and/or accommodating other portions of the fluid delivery system 10. In this exemplary embodiment, at the distal end 11 of the housing 20 may be an external interface notch 23 located proximate to a hydraulic assembly area 24 which may be located next to a trigger area 29. The trigger area 29 may extend from a pneumatic assembly area 26, which in turn may be proximate to a gas cartridge area 30 and a deflation area 31 near the proximal end of housing 20. Also closer to the proximal end 12 of the fluid delivery system 10 may be a handle portion 28 of the housing 20. The handle portion 28 may be have a soft grip insert molded into it. At the bottom of the handle portion 28, on the opposite side of the gas cartridge area 30 from the pneumatic assembly area 26, may be a receiving connector 27a which also serves as a lever connector 32. On top of the housing 20, located above the hydraulic cylinder area 24 and pneumatic assembly area 26, housing 20 defines an electronic interface opening 25.

Distributed throughout the housing portions 21, 22 may be structural supports or rib portions 33. These structural supports 33 may strengthen the housing 20, facilitate the production of the housing 20 by injecting molding or some other suitable production method known in the art, and/or serve as dividers for various areas in the housing portions. For example, the structural support 33a located at the distal end of the housing portions 21, 22 may separate the external interface notch 23 and its adjoining areas from the hydraulic assembly area 24, perhaps even providing a fluid tight and/or hermetical seal.

When housing portions 21, 22 are mated to enclose and/or include the various other components on the fluid delivery system 10, the system has a gun-like shape with a handle 28 to be held by a user. The inflation trigger 61 and deflation button 62 (to be described below) respectively accept the fore-finger and thumb of the user, with the remaining fingers of one user hand resting on the lever 64 (also to be described below). When system 10 is held in this way, the user can easily view electronic interface 40 and operate system 10.

The housing 20 may have various other alternative configurations. For example, the housing 20 is not limited to having two opposing portions, but may be made up of any number of housing portions configured and connected in any number of ways. Each housing portion may be formed by a variety of methods, for example, by injection molding of plastic or other suitable material. Various other configurations of features within the housing 20 and/or housing portions 21, 22 with respect to each other may also be desirable.

Figure 4A:
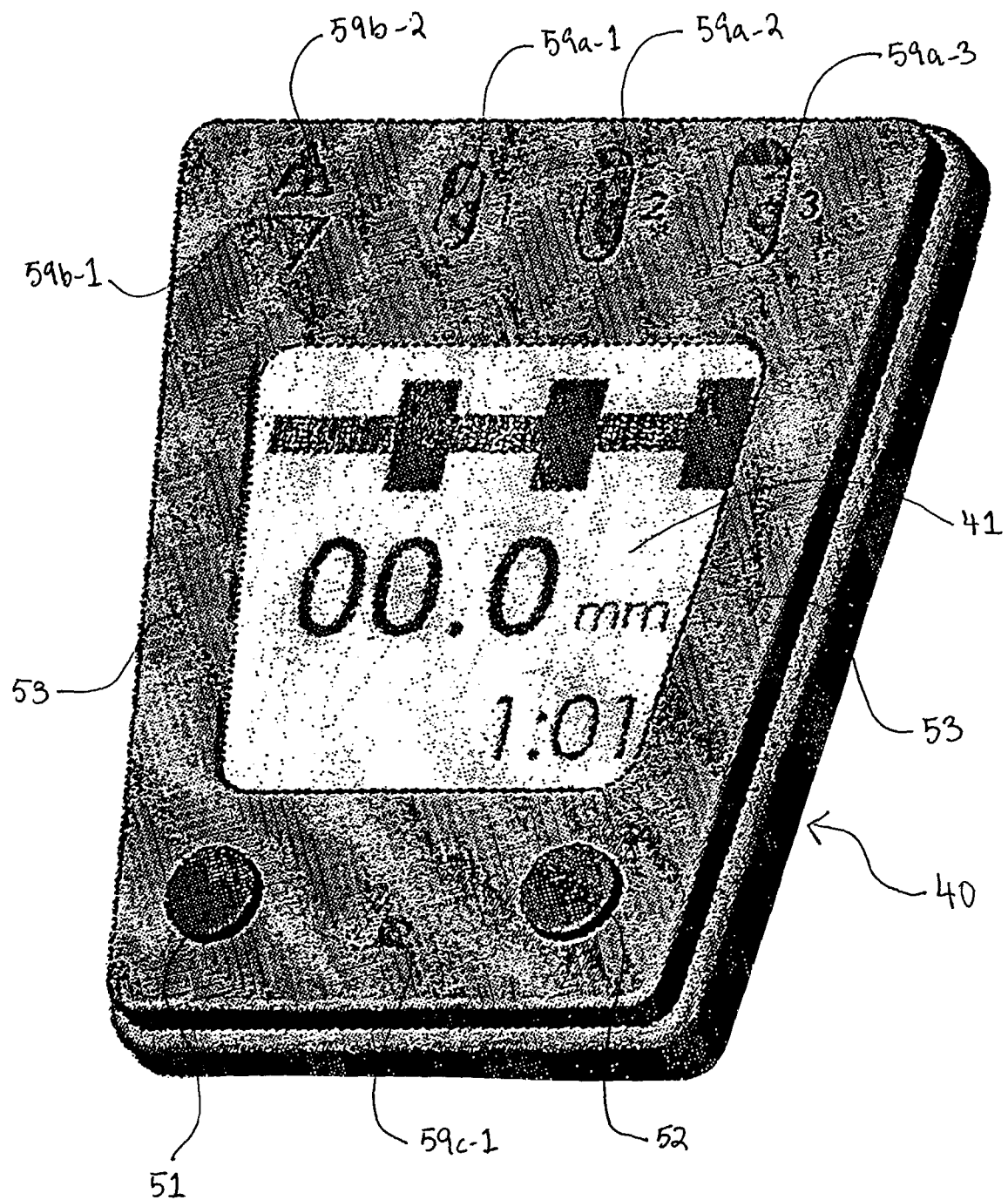
FIG. 4a is a perspective view of the electronic interface of the fluid delivery system of FIG. 1.
Figure 4B:
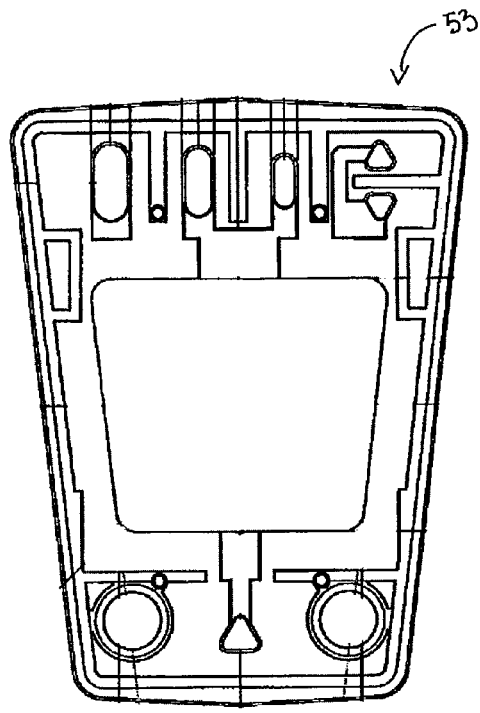
Figure 4C:
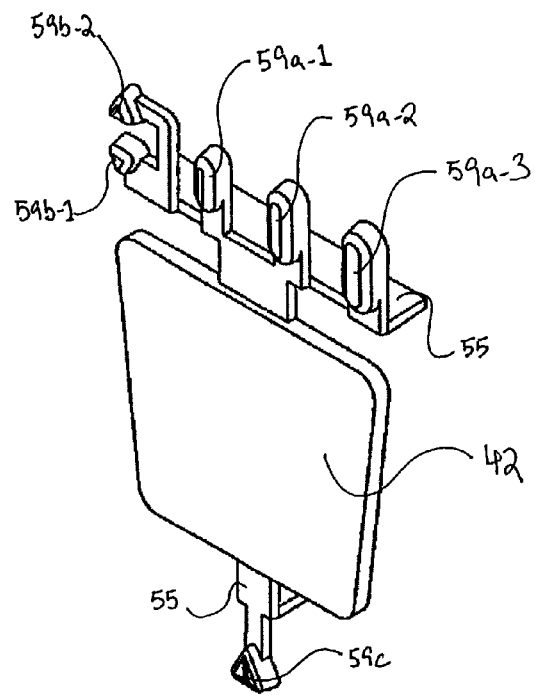
Figure 4D:
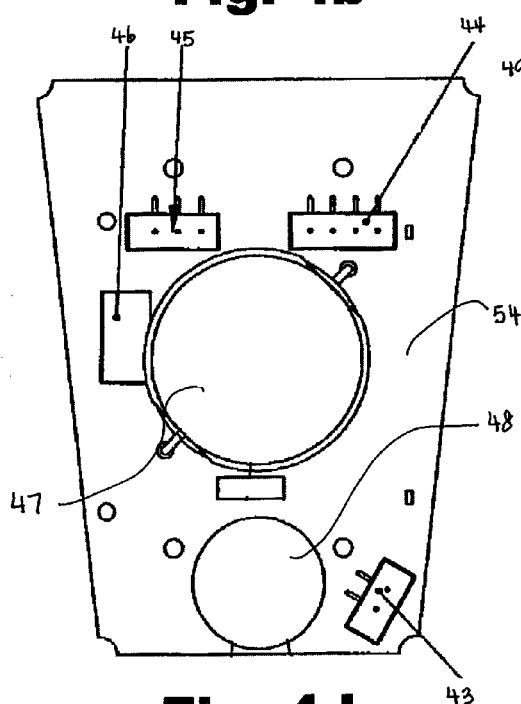

FIGS. 4a-4e depict an electronic interface 40 of an exemplary embodiment. Interface 40 sits within the electronic interface opening 25 defined by housing 20. As shown in these Figs., electronic interface 40 includes a housing 53 that contains an electronic interface frame 55 (FIG. 4c), an electronic interface board 54 (FIGS. 4d-4e), and operational buttons 51, 52 (FIG. 4a-4b). The housing 53 also defines a display portion 41 at the top and permits view of a plurality of lights 49 which may have corresponding light covers 59. Labels or other suitable graphics may be placed on the top of electronic interface 40.

Interface board 54 lies toward the bottom of housing 53. On a bottom side of the electronic interface board 54, as depicted, for example, in FIG. 4c, may be a plurality of circuit connectors for connection to other portions of the fluid delivery system 10. The circuit connectors include a programming test header 46, a deflate switch header 45, a pressure sensor header 44, and a power header 43. In various embodiments, the programming test header 46 may be connected to the display 41, the deflate switch header 45 may be connected to the deflate button 62 or the rapid depressurization valve, the pressure sensor header 44 may be connected to the pressure sensor subassembly 116, and the power header 43 may be connected to an external or internal power supply. On that same side of the electronic interface board 54 may also be a battery pack assembly 47 and an audio beeper 48. The electronic interface 40, and therefore its housing 53 and interface board 54, may be configured to use and/or facilitate the disposal and/or replacement of a battery in the battery pack assembly 47. The interconnection of the electrical components and their connection to sensors or other components within system 10 may be according to any suitable method known in the art.

Figure 4E:
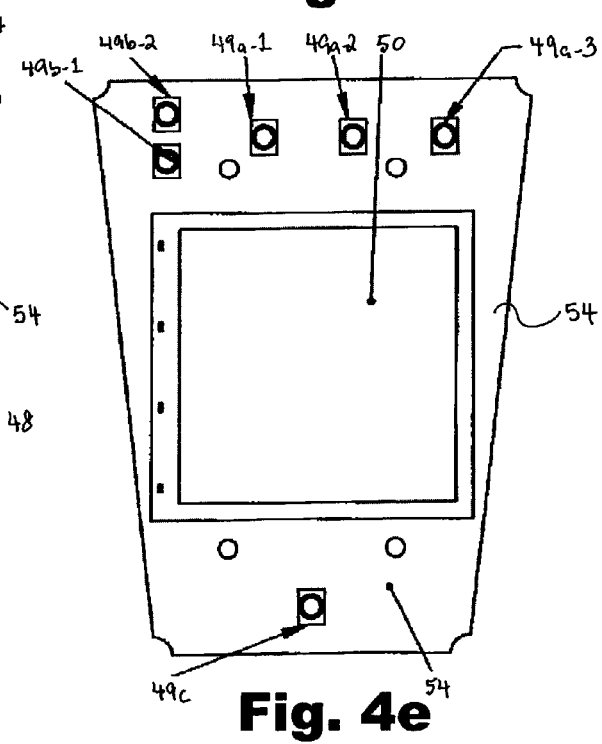

On the other, top side of the electronic interface board 54 (as shown in FIG. 4e) may be a plurality of lights 49, 50. The lights 49 may be light emitting diodes (LED) or any other suitable form of illumination. As depicted in the exemplary embodiment of FIG. 4d, there may be several groups of lights. One group of lights 49a may be indicate balloon inflation pressure and/or size. Using the embodiment where the fluid delivery system connects to a balloon dilatation catheter as a distal assembly, these lights 49a may indicate when the pressure in the balloon has reached a certain level, or when the balloon has reached a certain size. There may be three of these lights 49a-1, 49a-2, 49a-3, each corresponding to a different level of pressure or size that the balloon has reached. When used with other types of distal assemblies, lights 49a may indicate other suitable measures.

Another group of lights 49b may be directional indicator lights. Again, using the example of a balloon dilatation catheter as the distal assembly, lights 49b may indicate whether the balloon is increasing in pressure/size or decreasing in pressure/size. For example, the illumination of directional indicator light 49b-1 may indicate the pressure/size of the balloon is decreasing, while the illumination of directional indicator light 49b-2 may indicate the pressure/size of the balloon is increasing. All of the indicators 49, 50 may have various colors to indicate, for example, various pressures or errors.

Still another group of lights 49c may be error indicator lights. Once again using the embodiment with a balloon dilatation catheter, if the balloon is not inflating properly, the electronic interface 40 is not receiving signals properly, or any other error mode is detected, the error indicator light 49c may illuminate. Some other contemplated errors where lights 49c, or other error warnings on the electronic interface 40, may give an indication include leakage from either the hydraulic assembly 100 or pneumatic assembly 60, a sticky piston (i.e. primary piston 105 or the expansion piston 111) or valve, when the pressure readings are above or below a predetermined level, or when the battery is getting low.

It is also contemplated that substantially simultaneously with when certain indicator lights 49 are activated, the electronic interface may send signals to other parts of the fluid delivery system 10 to perform certain functions. For example, when a light 49a illuminates to indicate a certain balloon pressure/size, the electronic interface 40 may send a signal to the pneumatic assembly 60 to cease increasing gas pressure. Similarly, when the error light 49c illuminates, the electronic interface 40 may send a signal to the system to either shut down, or signal the rapid depressurization valve to rapidly depressurize the entire fluid delivery system 10.

The electronic interface board 54 may also have a backlight 50 that forms a part of the electronic display 41. This backlight 50 may be a liquid crystal display (LCD) showing text or other visual output itself, or it may illuminate the background of a text display so that the text can be more easily read.

Sandwiched in between the electronic interface housing 53 and the electronic interface board 54 may be an electronic interface frame 55. As depicted in the exemplary embodiment of FIG. 4b, this frame 55 may have a plurality of light covers 59, each corresponding to a light 49 on the electronic interface board. For example, the frame may have pressure/size indicator light covers 59a-1, 59a-2, 59a-3, corresponding respectively to pressure/size indicator lights 49a-1, 49a-2, 49a-3. The frame 55 may also have directional indicator light covers 59b-1, 59b-2 corresponding to directional indicator lights 49b-1, 49b-2. The frame may additionally have an error indicator light cover 59c corresponding to error indicator light 49c. The frame may also have a circuit holder lens 42. This circuit holder lens 42 may be a liquid crystal display (LCD) showing text or other visual output itself, or may be a screen that facilitates viewing of (and may also protect) the visual output on an electronic display 41, such as a cover. Frame 55 interconnects light covers 59 and the circuit lens holder 42.

In various embodiments, the display 41 may display, for example, gas pressure readings, fluid pressure readings, balloon size readings (for example, diameter and/or volume of the balloon) in the case of a balloon dilatation catheter, amount of fluid dispensed, amount of fluid in the fluid delivery system, whether any of the readings are changing, error indications, timer readings (for example, in the case a balloon dilatation catheter, how long the balloon has been inflated at a treatment site in the body), temperature readings, whether any of the readings have reached a predetermined value, bar graphs that correspond to the readings, a power on indication, or any other desired measurement or reading depending on the particular application.

In an exemplary embodiment, the buttons 51, 52 may respectively be a mute button 51 and a power button 52. The mute button 51 may be for silencing the audio beeper 48, for example, when the indicators 49a light up when they reach a certain level or when the error indicator 49c is illuminated. The power button 52 may be for powering up the electronic interface 40, for example, prior to the use of the device.

The electronic interface 40 may have various alternative configurations. For example, the electronic interface 40 may not be integral with the top of housing 20 and instead may be integral with another portion or side of housing 20. In another embodiment, interface 40 may not be integral with housing 20 at all, instead being connected to housing 20 by other means.

In another example, the various electrical components that make up the electronic interface 40 may be individually distributed throughout the housing. In yet another example, the electronics housing portion 53 may be a plurality of electronics housing portions. Different configurations of the components on the electronic interface board 54 are also contemplated. In addition, the components may be arranged on multiple circuit boards and/or not on circuit boards and joined, for example, through wire connections. In still another example, the light covers 59 and circuit lens holder 42 may be configured together into various subcomponents, or may be individual pieces either sandwiched between the electronic interface housing 53 and electronic interface board 55 or distributed throughout the electronic interface 40.

In addition, the features for display on display 41 or other portions of the electronic interface 40 are exemplary and any other features consistent with the use of the fluid delivery system 10 may also be displayed. For example, one of the buttons 51, 52 may be for initiating a timer displayed on the display, or the electronic interface may have more buttons 51, 52 to perform other functions. In another embodiment, in addition to or as an alternative to buttons 51, 52, command inputs could be by voice command, by a footswitch, or by software on an associated computer interface. In addition, the output may also by software associated on a computer interface, or by mechanical instead of electrical components, for example, gages and poppets. In a further embodiment, the electronic interface 40 may function until one of the readings reaches a predetermined value, cease functioning in that all the outputs on the electronic interface (i.e. display 41, indicators 49, 50) remain fixed, and remain fixed until a restart command, for example a further actuation of the pneumatic valve, is given. The electronic display 40 could also send or receive data via telemetry.

Figure 5A:
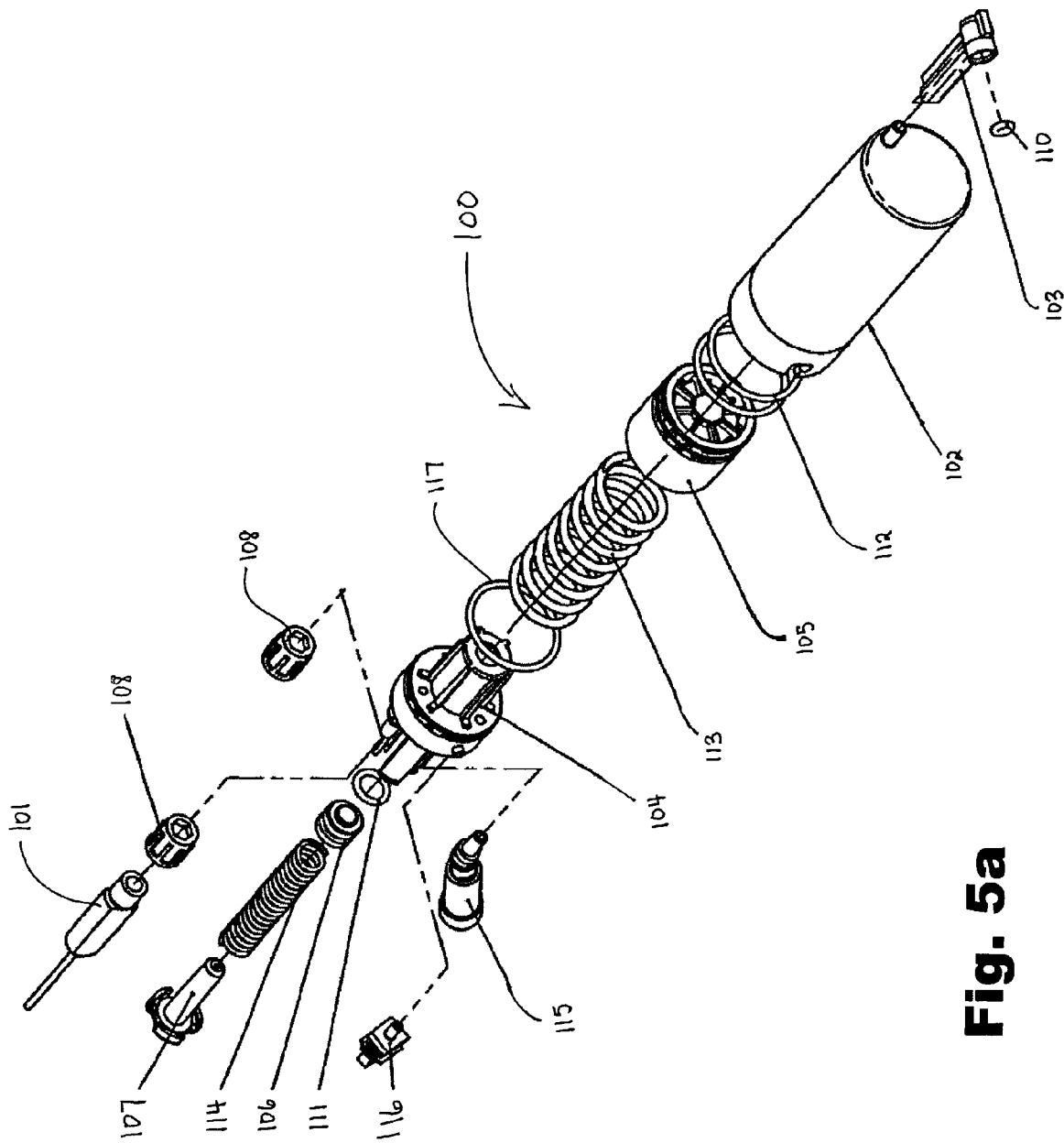
FIG. 5a is a perspective exploded view of various parts that comprise a hydraulic assembly of the fluid delivery system of FIG. 1.
Figure 5B:
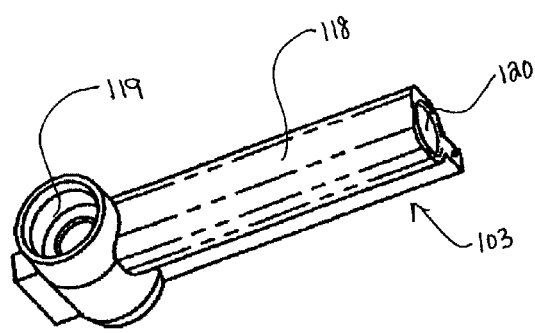
Figure 5C:
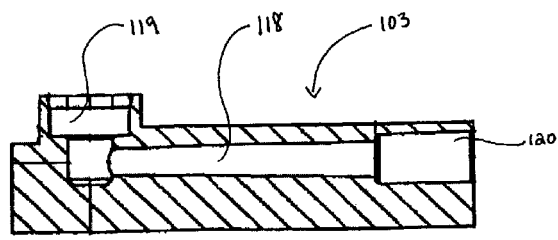
FIG. 5c is a cross-sectional view of a hydraulic stem of the hydraulic assembly of FIG. 5b.
Figure 5N:
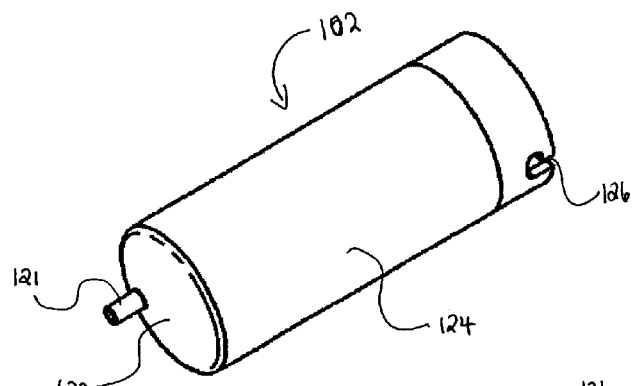
Figure 5O:
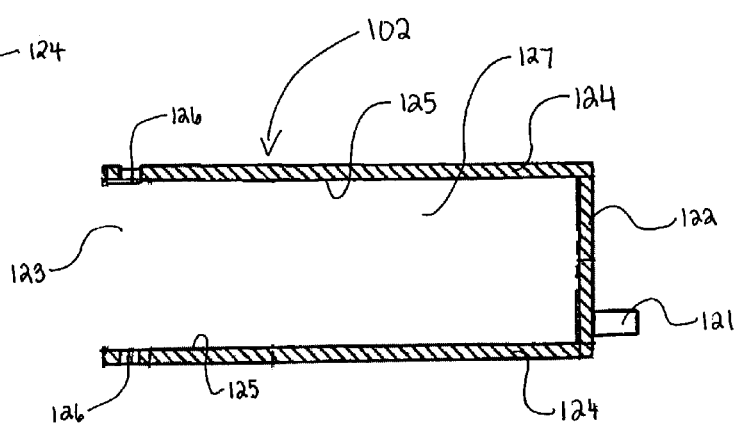
FIG. 5o is a cross-sectional view of a hydraulic cylinder of the hydraulic assembly of FIG. 5n.

FIGS. 5a-5o show the hydraulic assembly 100 and its components of an exemplary embodiment. In an exemplary embodiment, the hydraulic assembly 100 may be configured to contain 30 cubic centimeters of fluid, for example, to be capable of inflating a balloon of a balloon dilatation catheter. Other size assemblies are within the scope of the invention and depend on the particular application and need for fluid. The hydraulic assembly 100, portions of the hydraulic assembly 100 containing fluid, or other fluid containers may be termed reservoirs.

Beginning at the distal end of the hydraulic assembly 100 and with specific reference to FIG. 5a, the hydraulic stem 103 connects to the fluid connector 67 on the pneumatic assembly 60 (to be described below). The hydraulic stem 103 then connects to the hydraulic cylinder 102, which contains the primary piston 105. The primary piston 105 then connects to or is at least in contact with a primary piston spring 113. The primary piston spring 113 connects to or is at least in contact with the hydraulic cap 104. The hydraulic cap 104 in turn connects to or is at least immobilized relative to the hydraulic cylinder 102. Connected to the hydraulic cap 104 may be a check valve 115 and at least one luer hub 108 which may connect to external interface 101. The hydraulic cap 104 may also contain an expansion piston 106. The expansion piston 106 connects to or is at least be in contact with an expansion piston spring 114, which at an opposite end connects to or is at least in contact with a spring retainer 107.

An exemplary embodiment of the hydraulic stem 103 is depicted in FIGS. 5b-5c. The hydraulic stem 103 may comprise a pneumatic interface 119 that connects to the fluid connector 67 of the pneumatic assembly, a hydraulic cylinder interface 120 that connects to the hydraulic cylinder 102, and a hydraulic stem shaft 118 that connects the pneumatic interface 119 to the hydraulic cylinder interface 120. In the exemplary embodiment, the central axes of the interfaces 119, 120 are perpendicular to each other and the shaft 118 is linear. It is contemplated that the pneumatic interface 119 and the fluid connector 67 may move axially with respect to each other so as to better facilitate, for example, ease of use, ease of connection, and/or freedom of movement.

The junction/interface between the hydraulic stem 103 and the pneumatic valve 70 through the pneumatic interface 119 and the fluid connector 67 may include a hydraulic stem O-ring 110 to facilitate a fluid tight and/or hermetical seal between the two members, and also to prevent the buildup of gas pressure from destroying the junction/interface. To receive the hydraulic stem O-ring 110, the inner surface of the pneumatic interface 119 may be chamfered. The hydraulic stem O-ring 110 may also facilitate better axial movement between the pneumatic interface and the fluid connector while still maintaining the fluid tight and/or hermetical seal.

The interface between the hydraulic cylinder interface 120 and hydraulic stem interface 121 of the hydraulic cylinder 102 may also have an O-ring to facilitate the creation of a fluid tight and/or hermetical seal and also to prevent the buildup of gas pressure from destroying the junction/interface. In the exemplary embodiment, the pneumatic interface 119 may have a configuration or shape to receive the fluid connector 67, and the hydraulic stem interface 121 may have a configuration to receive the hydraulic cylinder interface 120.

An exemplary embodiment of the hydraulic cylinder 102 is depicted in FIGS. 5n-5o. Hydraulic cylinder 102 may have a fluid chamber 127 bounded by a proximal wall 122, at least one sidewall 124, and a distal opening 123. The hydraulic stem interface 121 may be connected to or integral with the proximal wall 122, and may be in fluid communication with the fluid chamber 127. The sidewall 124 may also have locking parts 126 located adjacent to the distal opening 123 of the hydraulic cylinder 102. The locking parts 126 may be configured to receive a corresponding locking part 157, for example, disposed on the hydraulic cap 104. The inner surface 125 of the sidewall 124 may be smooth or otherwise configured to facilitate the movement of members within the hydraulic cylinder 102, for example, the primary piston 105 or the primary piston O-rings 112. The hydraulic cylinder 102 may be made of a material that can withstand high internal/external fluid and/or gas pressures.

Figure 5L:
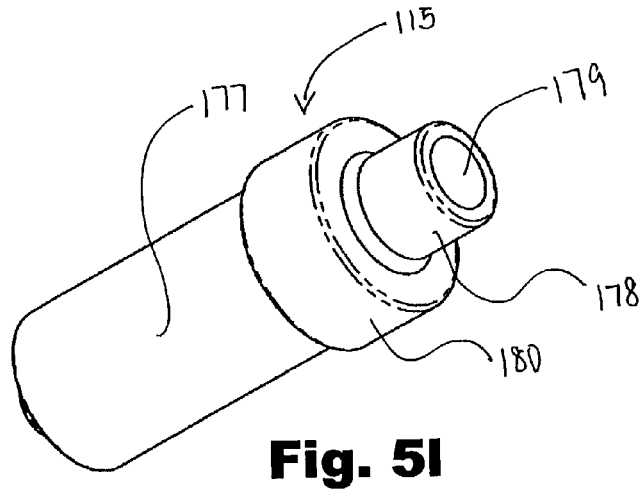
Figure 5M:
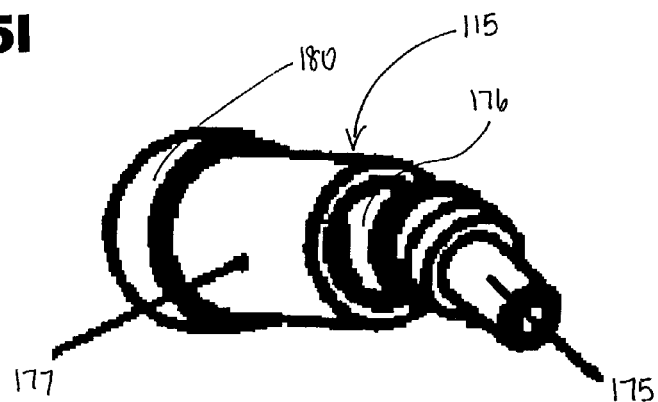
Figure 5D:
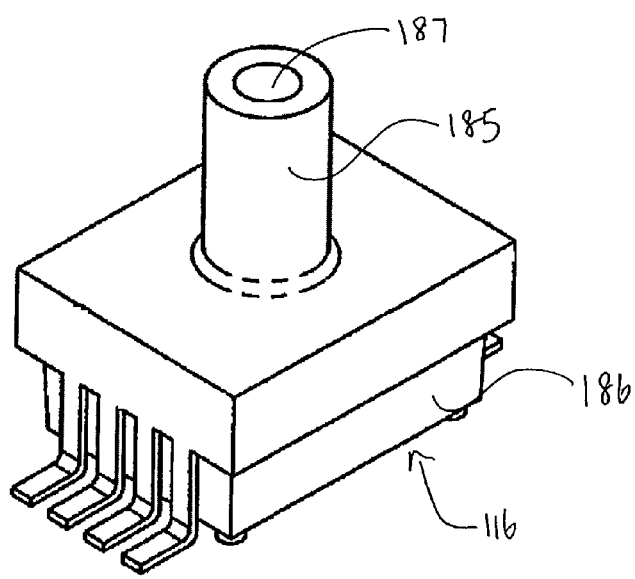
Figure 5E:
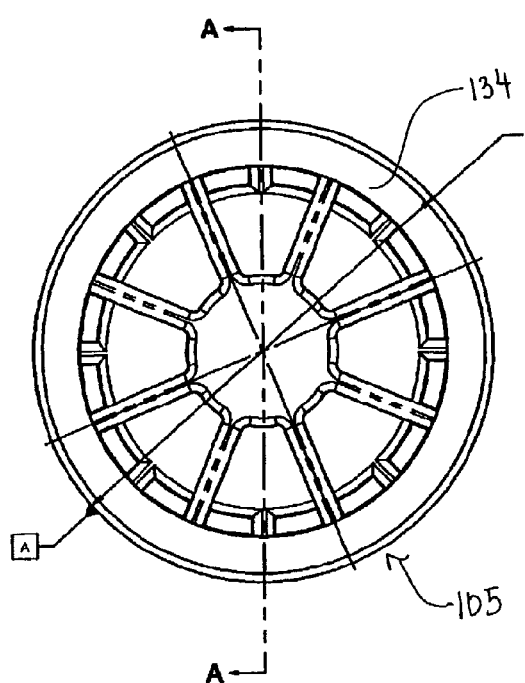
Figure 5F:
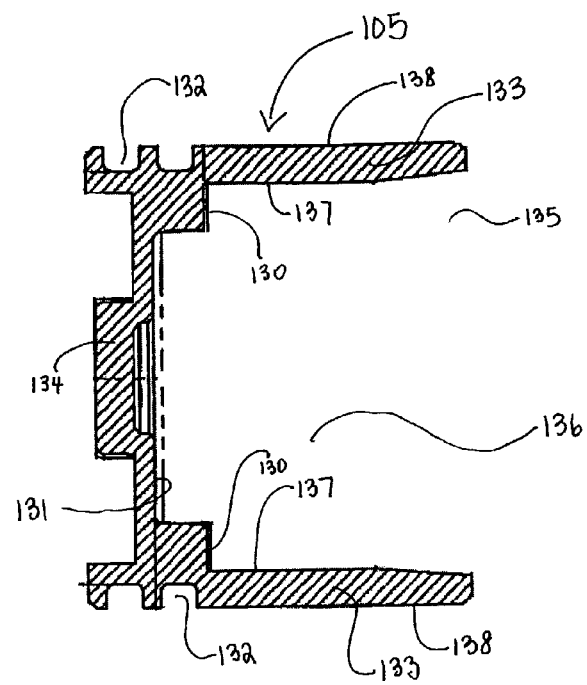
FIG. 5f is a cross-sectional view along line A-A of FIG. 5e.

An exemplary embodiment of the primary piston 105 is depicted in FIGS. 5e-5f. The primary piston 105 has a fluid chamber 136 which is in fluid connection with at least a part of the fluid chamber 127 of the hydraulic cylinder 102. The fluid chamber 136 is bounded by a proximal wall 134, at least one side wall 133, and a distal opening 135. The inner surface 137 of the primary piston 105 may define at least one spring receiver surface 130 and a hydraulic cap receiver surface 131. The spring receiver surface 130 may be configured to receive or at least contact a portion of the primary piston spring 113, and may also be configured to be sturdy enough so that force of the primary piston spring 113 does not substantially deform or break the primary piston. The hydraulic cap receiver surface 131 may also be configured so that when the primary piston spring 113 reaches its maximum point of collapse or compression, the proximal end 140 of the hydraulic cap 104 may be substantially flush with the hydraulic cap receiver surface 131.

The primary piston 105 may have a plurality of primary piston O-rings 112 wrapped around its outer surface 132 to facilitate both a fluid tight and/or hermetical seal with the inner surface 125 of the hydraulic cylinder 102, but also may serve as a friction reducing body so as to allow the primary piston 105 to slide relatively freely and easily within the hydraulic cylinder 102. On the outer surface 138 of the primary piston 105 may be at least one O-ring receiver or groove 132. These O-ring receivers 132 may receive at least one primary piston O-ring 112.

Figure 5J:
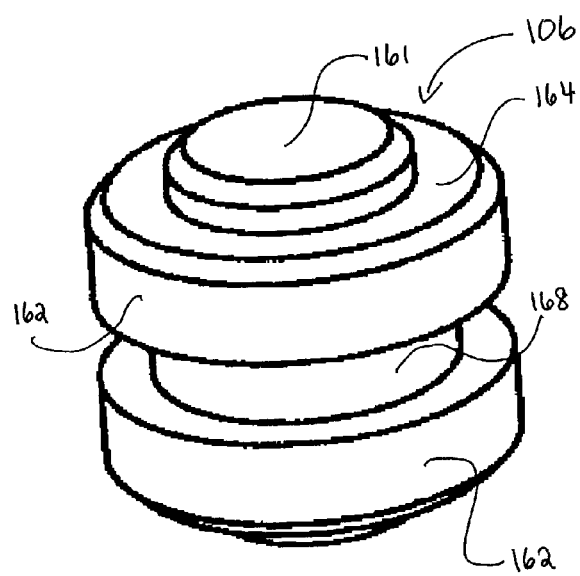
Figure 5K:
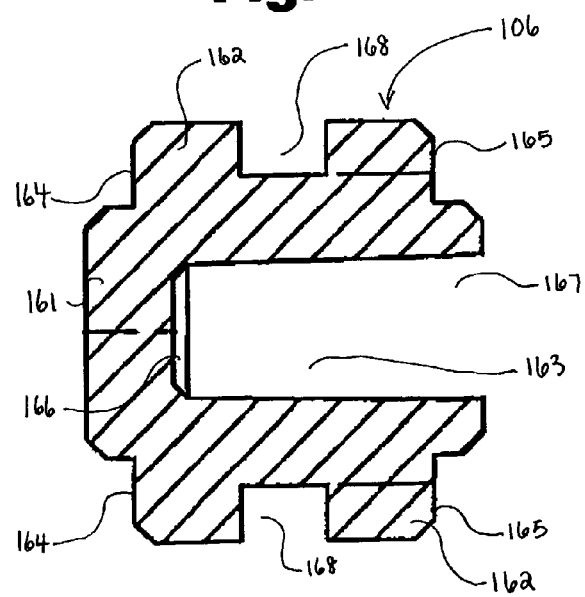
FIG. 5k is a cross-sectional view of the expansion piston of FIG. 5j.
Figure 5G:
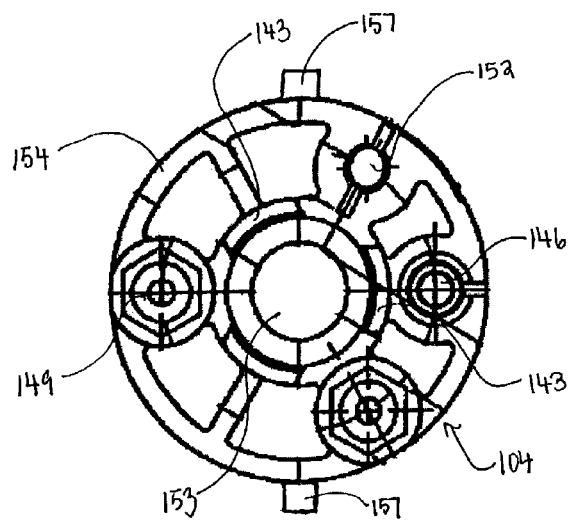
Figure 5H:
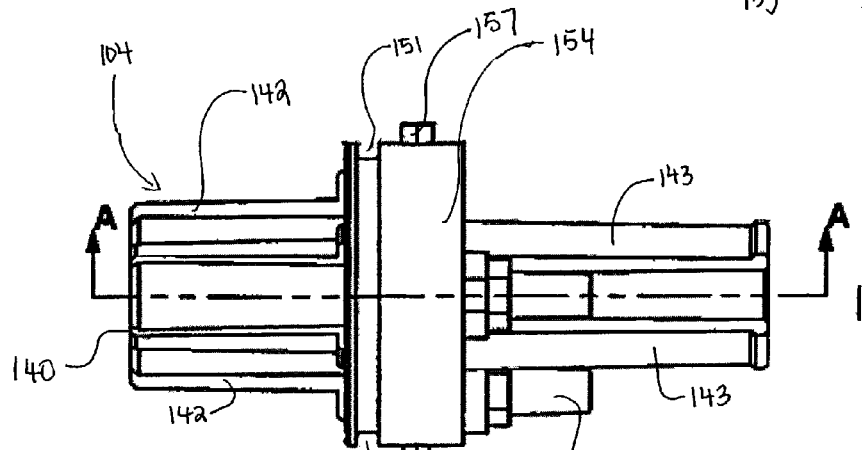
Figure 5I:
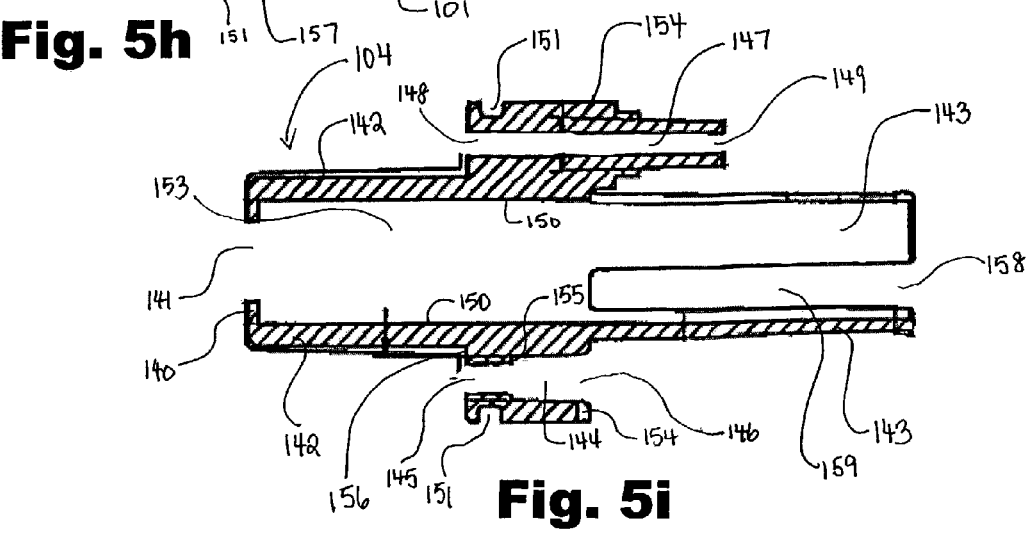

An exemplary embodiment of the hydraulic cap 104 is depicted in FIGS. 5g-5i. Hydraulic cap 104 may have a proximal end 140 defining a proximal opening 141. The proximal opening 141 may allow at least portions of an inner chamber 153 of the hydraulic cap 104 to be in fluid communication with at least a portion of the fluid chamber 127 of the hydraulic cylinder 102. The proximal end 140 may be connected to proximal sidewall 142, which may in turn be connected to the central portion 154 of the hydraulic cap 104. The inner chamber 153 may be bounded by the proximal opening 141, the inner surfaces 150 of proximal sidewall 142, the central portion 154, distal protrusions 143, a distal opening 158, and distal gaps 159 between the distal protrusions 143.

The central portion 154 of the hydraulic cap 104 has many features. For example, the central portion 154 may have a check valve connector 144, which may have on one end a proximal opening 145 in fluid communication with at least a portion of the fluid chamber 127 of the hydraulic cylinder 102, and on the other end a distal opening 146 configured to be connected to and/or be in fluid communication with a check valve 115.

The central portion 154 also may have an external interface connector 147. The external interface connector 147 may have on one end a proximal opening 148 in fluid communication with at least a portion of the fluid chamber 127 of the hydraulic cylinder 102, and on the other end a distal opening 149 configured to be connected to and/or be in fluid communication with the external interface 101. In the alternative, the external interface connector 147 may be configured to connect to or receive at least one luer hub 108, with the luer hubs 108 in turn connecting with the external interface 101.

Also disposed on the central portion 154 of the hydraulic cap 104 may be a pressure sensor port 152, which may be configured to receive a pressure sensor subassembly 116. A hydraulic cap O-ring 117 may be wrapped around a portion, for example the central portion 154, of the hydraulic cap 104 so as to facilitate an air-tight seal between the hydraulic cap 104 and the inner surface 125 of the of hydraulic cylinder 102. The central portion 154 may also have at least one O-ring receiver or groove 151 to facilitate receipt and retention of the hydraulic cap O-ring 117.

The proximal sidewall 142, central portion 154, and distal protrusions 143 may all be connected and, for example, be formed as a single piece. The distal protrusions 143, as depicted in the exemplary embodiment shown in FIGS. 5g-5i, are about one-half the length of the hydraulic cap 104 and cover roughly one-half of the circumference of the hydraulic cap, with each individual distal protrusion 143 covering about one-sixth of the circumference and being equally spaced from each other. The distal protrusions 143 may be configured to retain, for example, an expansion piston 106 within the inner chamber 153 adjacent to the protrusions 143. The inner surface 150 of the hydraulic cap 104 may run almost the entire length of the hydraulic cap 104, so that it can accommodate, for example, the movement of an expansion piston 106 along almost the entire length of the hydraulic cap 104, for example, from the proximal opening 141 on the proximal end 140 to the distal opening 158.

The hydraulic cap 104 may also have a locking part 157 configured to lock with, for example, the locking part 126 on the hydraulic cylinder 102. In an exemplary embodiment, the hydraulic cap 104 and hydraulic cylinder 102 are locked together and form a fluid tight and/or hermetical seal such that no fluid escapes from the fluid chamber 127 through a potential gap in the distal opening 123 between the hydraulic cap 104 and the hydraulic cylinder 102. The locking parts 126, 157 may also be configured to keep the hydraulic cylinder 102 and hydraulic cap 104 together under internal/external gas and/or fluid pressures.

FIGS. 5j-5k depict an exemplary embodiment of the expansion piston 106. The expansion piston 106 may have a inner chamber 163 that is bounded by a proximal wall 161, sidewalls 162, and a distal opening 167. Adjacent to the junction of the proximal wall 161 and sidewall 162 may be an O-ring receiver or groove 164 for accommodating the expansion piston O-ring 111. The expansion piston O-ring 111 may facilitate both an air-tight seal between the expansion piston 106 and the hydraulic cap 104, as well as reducing friction with the inner surface of the hydraulic cap 104. On the portion of the sidewall 162 opposite the O-ring receiver 164, and adjacent to the distal opening 167, may be a spring receiver or groove 165 configured to accommodate the receipt and retention of an expansion piston spring 114. Located between the spring receiver 165 and O-ring receiver 164 along the sidewall 162 may be a central groove 168. This central groove 168 may be configured to receive and/or retain an additional expansion piston O-ring, and/or may serve any other suitable function. At the proximal end of the inner chamber 163 along the proximal wall 161, and adjacent to the sidewall 162, may be a chamfered proximal end 166, which may be configured to receive the proximal end of a spring retainer 107, should the expansion piston spring 114 reach its maximum desired compression.

FIGS. 5l-5m depict an exemplary embodiment of the check valve 115 that may be connected to the check valve connector 144 on the hydraulic cap 104. The check valve 115 may have a hydraulic cap interface 175 which may be configured to be inserted into the distal opening 146 on the check valve connector 144. To accommodate the check valve 115, the check valve connector 144 may have a recess 155 configured to receive the proximal end of the hydraulic cap interface 175 and prevent further insertion of the hydraulic cap interface 175 into the hydraulic cap 104.

The hydraulic cap interface 175 may be connected to the valve chamber 177 of the check valve 115 through a flexible interface extension 176, so that the axes of the hydraulic cap interface 175 and valve chamber 177, respectively, are not coaxial, and may instead be oriented in different directions. The hydraulic cap interface 175 may also be configured to withstand pressure from the hydraulic cap 104 to be blown off when the fluid pressure builds in the fluid chamber 127.

On the side of the valve chamber 177 opposite the hydraulic cap interface 175 may be a valve cap 180 which may include an external interface portion 178, which in turn may have an external interface opening 179 which leads into the valve chamber 177. The interior of the valve chamber 177 may be configured to at least initially maintain a fluid tight and/or hermetical seal, and even if pressure is exerted from the hydraulic cap interface 175 side of the valve chamber 177, the check valve 115 could still maintain its seal. However, if pressure is exerted from the external interface 178 through the valve cap 180 into the valve chamber 177, the interior of the valve chamber 177 may be configured to accept fluid flow (for example, fluid for the balloon dilator) from the external interface 178, through the valve chamber 177, through the hydraulic cap interface 175, and into the valve chamber 177. Additionally, the interior of the valve chamber 177 may also be configured so that if a user wished to eliminate the fluid tight and/or hermetical seal, and allow fluid to flow in the direction from the hydraulic cap interface 175 through the valve chamber 177, the user could, for example, remove the valve cap 180, or introduce a foreign object into the external interface opening 179 and dislodge and/or puncture the portion of the check valve 115 that is configured to maintain the fluid tight and/or hermetical seal.

FIG. 5d depicts an exemplary embodiment of the pressure sensor subassembly 116. The pressure sensor subassembly 116 has a hydraulic cap interface 185 which may be connected to the hydraulic cap 104, for example, by placing hydraulic cap interface 185 into the pressure sensor port 152. The hydraulic cap interface 185 of the pressure sensor subassembly 116 may form a fluid tight and/or hermetical seal with the pressure sensor port 152 so as to facilitate the accurate measurement of the fluid pressure within the hydraulic cylinder 102. The pressure sensor subassembly may also have an electronics housing 186 which has circuits or other means for measuring the fluid pressure within the hydraulic cylinder 102, and the electronics housing 186 may also have means to relay information, pressure or otherwise, to electronic interface 40, for example, for display or use in triggering other functions of the system 10. The hydraulic cap interface 185 may also be configured to withstand being blown out of the pressure sensor port 152 due to pressure increases in the fluid chamber 127, or in another embodiment, from gas pressure.

The hydraulic assembly may have various alternate configurations. Any hydraulic assembly that accepts a gas pressure input, and in response to that gas pressure input, outputs fluid from the hydraulic assembly may be acceptable. In addition, no specific fluid capacity of the hydraulic assembly is required or necessary, as the fluid capacity depends on the particular application.

As additional examples of modifications of the hydraulic assembly, the central axes of the interfaces 119, 120 of the hydraulic stem 103 may not be perpendicular to each other and the shaft 118 may not be linear. In addition, the fluid connector 67 on the pneumatic valve 70 may be directly connected to the hydraulic stem interface 121 of the hydraulic cylinder 120, possibly with an O-ring in between. Furthermore, the hydraulic assembly 100 and/or pneumatic assembly 60 may have a internal nozzles to concentrate fluids in various portions of the system. In an additional example, the hydraulic cylinder could be a collapsible sac 102 that may be configured to rebound as well, for example, through the utilizaton of elastomeric walls or by building springs into the walls.

In yet another example, the spring receiver 130 of the primary piston 105 may be located distally from the hydraulic cap receiver 131 relative to the proximal wall 134, the spring receiver 130 and hydraulic cap receiver 131 may actually share the same flat surface portion of the inner surface 137. In addition, the primary piston spring 113 and/or the hydraulic cap 104 may be configured so that the hydraulic cap 104 never comes into contact with the hydraulic cap receiver 131. Along those lines, the pistons 105, 111 and fluid reservoirs in the hydraulic assembly 100 could be configured so that the pistons 105, 111, no matter what the fluid pressure, are never bounded by portions of the hydraulic assembly 100 so that movement is prevented in either direction. This may be preferable so that the fluid delivery system 10 could be put in inflation mode or deflation mode at any point in time without consideration of space and movement limitations.

In still another example, the features disposed on the hydraulic cap 104, such as the check valve 115 and pressure sensor subassembly 116, may be located on other suitable portions of the hydraulic assembly 100 or pneumatic assembly 60. For example, the check valve may be connected to the hydraulic cylinder 102, the external interface 101, or some other suitable portion of the hydraulic assembly 100 that, for example, allows fluid communication with the fluid chamber 127. In another example, the pressure sensor subassembly 116 may be connected to the hydraulic cylinder 102 or the external interface 101, or any other portion of the hydraulic assembly 100 or pneumatic assembly 60 where it can measure, for example, fluid and/or gas pressure. In general, the various portions of the hydraulic assembly 100 may be spread out in various portions of the fluid delivery system 10, and may be connected by hydraulic lines.

In another example, the expansion piston 106 and expansion piston spring 114 assembly may in fact be any system configured to store potential energy during the ejection of fluid from the fluid delivery system 10, and release energy following the end of the ejection of the fluid from the fluid delivery system 10. The expansion piston 106 may also be made of a compressible material, for example, so as to completely fill the cross-sectional area of the inner chamber 153 of the hydraulic cap 104, or to give additional compression to the system so as to store more potential energy.

FIGS. 6a-6e depict portions of an exemplary embodiment of the pneumatic assembly 60. The pneumatic assembly 60 may be located inside the handle portion 28 of the housing 20. Components of pneumatic assembly 60, shown in FIGS. 1, 2 and 6a-6e, include a pneumatic valve 70, a deflation button 62, a gas cartridge 63, and a lever 64. The pneumatic assembly 60 may also comprise a rapid depressurization valve 91.

FIGS. 6a-6d depict an exemplary embodiment of the pneumatic valve 70. The pneumatic valve 70 may comprise a pneumatic valve base 71 with a relief cap 90, an inflation trigger 61, and a gas cartridge interface 66 connected to various portions of the pneumatic base 71. The pneumatic valve 70 may also have a rapid depressurization valve. Additionally, a lever 64 may be simultaneously connected to the inflation trigger 61 and the lever connector 32 on the housing 20. Furthermore, a gas cartridge 63 may be connected, in a fluid tight and/or hermetical manner, to the gas cartridge interface 66.

The relief cap 90 includes a deflation interface 65 that when combined with the other parts of the fluid delivery system 10, may connect with or at least contact the deflation button 62. In one exemplary embodiment, the depression of the deflation button 62 may cause the movement of the deflation interface 65 away from the relief cap 90 which in turn may cause the relief cap 90 to discharge gas, for example, through a gap in the junction between the deflation interface 65 and the relief cap 90, through a relief gap 187 disposed between a grooved portion 72 of the pneumatic valve 70 and a grooved portion 186 of the relief cap 90, or through some other portion of the relief cap 90. In the exemplary embodiment, the relief cap 90 is held onto a relief cap portion 488 of the pneumatic valve base 71 by being threaded onto the pneumatic base 71, for example, through the interlocking of the grooved portion 72 of the pneumatic valve 70 and the grooved portion 186 of the relief cap 90. However, in another example, the relief cap 90 may be held onto the pneumatic valve base 71 by the housing portions 21, 22, or by some other fastening means. The relief cap 90 may also have portions near its proximal end 190 configured to retain or at least be in contact with a relief spring 165. The relief spring 165 may be disposed around, for example, the deflation valve legs 188 of the deflation valve 166, and have one end retained by or at least in contact with a relief spring receiver portion 191 of the deflation valve 166.

In an exemplary embodiment, the relief cap may include the deflation interface 65 integral with a deflation shaft 160 which may in turn be integral with a deflation ball interface 163. The deflation ball interface 163 may have deflation shaft positioners 162 which may keep the deflation ball interface 163 and the deflation shaft 160 centered in the relief cap 90 and/or the relief cap interface chamber 76 of the pneumatic valve 70. The deflation shaft positioners 162 may keep those relief cap portions centered by virtue of its interaction with the deflation valves legs 188 which may be connected to the deflation valve 166, for example, acting as spring-like elements which may allow, given external pressures, movement of the deflation ball interface 163 and deflation shaft 160 relative to the pneumatic valve 70. The deflation shaft positioners 162 may be rigid enough so that in the absence of external pressures, it biases the deflation ball interface 163 and deflation shaft 160 to their original locations. The deflation valve legs 188 may also have deflation leg receiver 194 that, when moved far enough toward the proximal end 190 of the relief cap 90, may come into contact with the shaft positioner receivers 193 disposed on the deflation valve legs 188 and prevent further movement of the deflation shaft 160 and the deflation ball interface 162 toward the proximal end 190 of the relief cap 90. The deflation shaft 160 may also have a deflation spring receiver 189 for retaining or at least being in contact with an end of a deflation spring 161. The deflation spring 161 may be disposed around the deflation shaft 160 and extend to almost the deflation interface 65, being retained or at least in contact with a proximal end 190 of the relief cap 90.

The deflation valve 166 may be lodged against a chamfered deflation valve receiver portion 192 that is disposed in the relief cap interface chamber 76 of the pneumatic valve 70. The deflation valve O-ring 168 may be lodged between the deflation valve 166 and the chamfered deflation valve receiver portion 192 of the pneumatic valve base 71 and may provide a fluid tight and/or hermetical seal. The deflation valve 166 may have within it a deflation valve passage 167 extending, for example, along a central axis and configured to facilitate fluid communication between the fluid transfer chamber 73 and portions of the relief cap interface chamber 76 disposed between the deflation valve legs 188. Lodged between the proximal end of the deflation valve passage 167 of the deflation valve 166 and the deflation ball interface 163 may be a deflation ball 164 which, depending on its position, may facilitate or impede fluid communication between the between the fluid transfer chamber 73 and portions of the relief cap interface chamber 76 disposed between the deflation valve legs 188.

In another exemplary embodiment, the relief cap 90, or other portion of the pneumatic assembly 60 may comprise a rapid depressurization valve connected to a rapid depressurization button, where the user may, by pressing the button, rapidly depressurize the pneumatic assembly. The relief cap 90 may also have high pressure valves 91, for example, a spring activated poppet valve 91, that regulates the maximum pressure in the pneumatic assembly 60. The poppet valves 91 may be configured to have a poppet ball lodged in the interface portion of the poppet valve 91 which is in fluid communication with the relief cap interface chamber 76. The poppet ball may be held against the interface portion of the poppet valve 91 by a poppet spring. The poppet spring may be calibrated to hold the poppet ball in the interface portion of the poppet valve 91 with an appropriate amount of force such that only when the pressure in the relief cap interface chamber 76 reaches a predetermined maximum level will the poppet spring compress, the poppet ball move away from the interface portion, and thus the relief cap interface chamber 76 be in fluid communication with the external environment via the poppet valve 91.

Figure 6A:
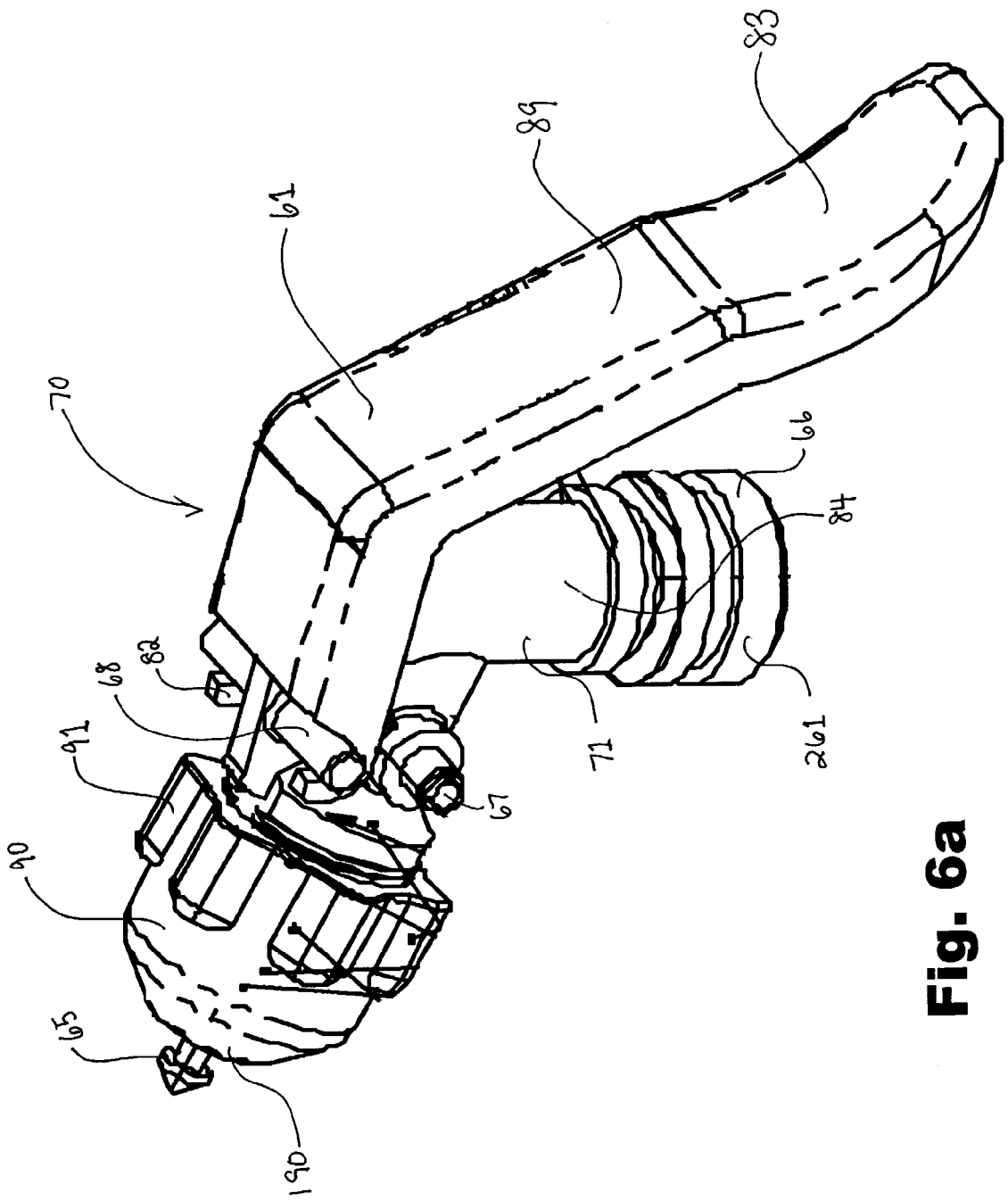
FIG. 6a is a perspective view of a portion of a pneumatic assembly of the fluid delivery system of FIG. 1.
Figure 6E:
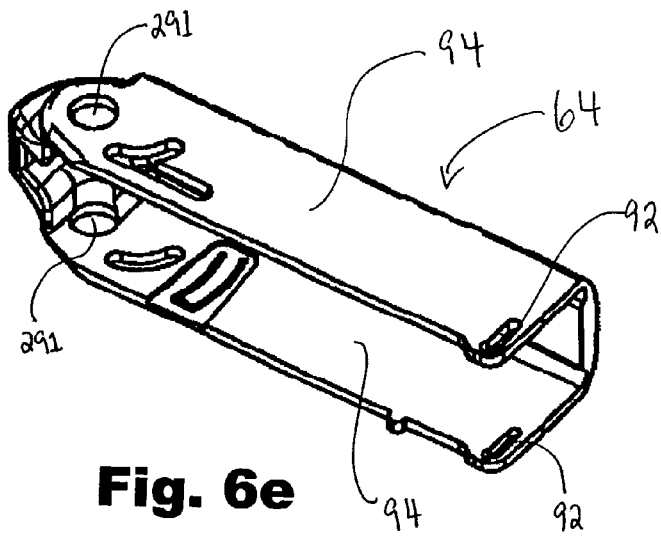
Figure 6B:
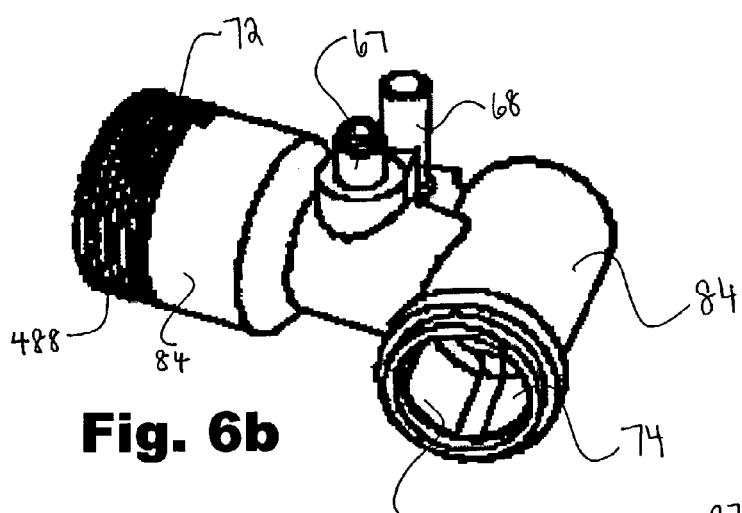
Figure 6C:
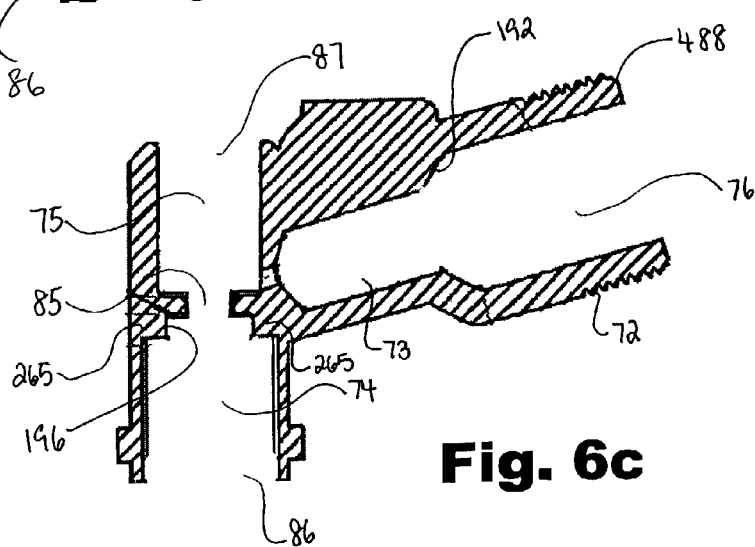
FIG. 6c is a cross-sectional view of the pneumatic valve of FIG. 6b.
Figure 6D:
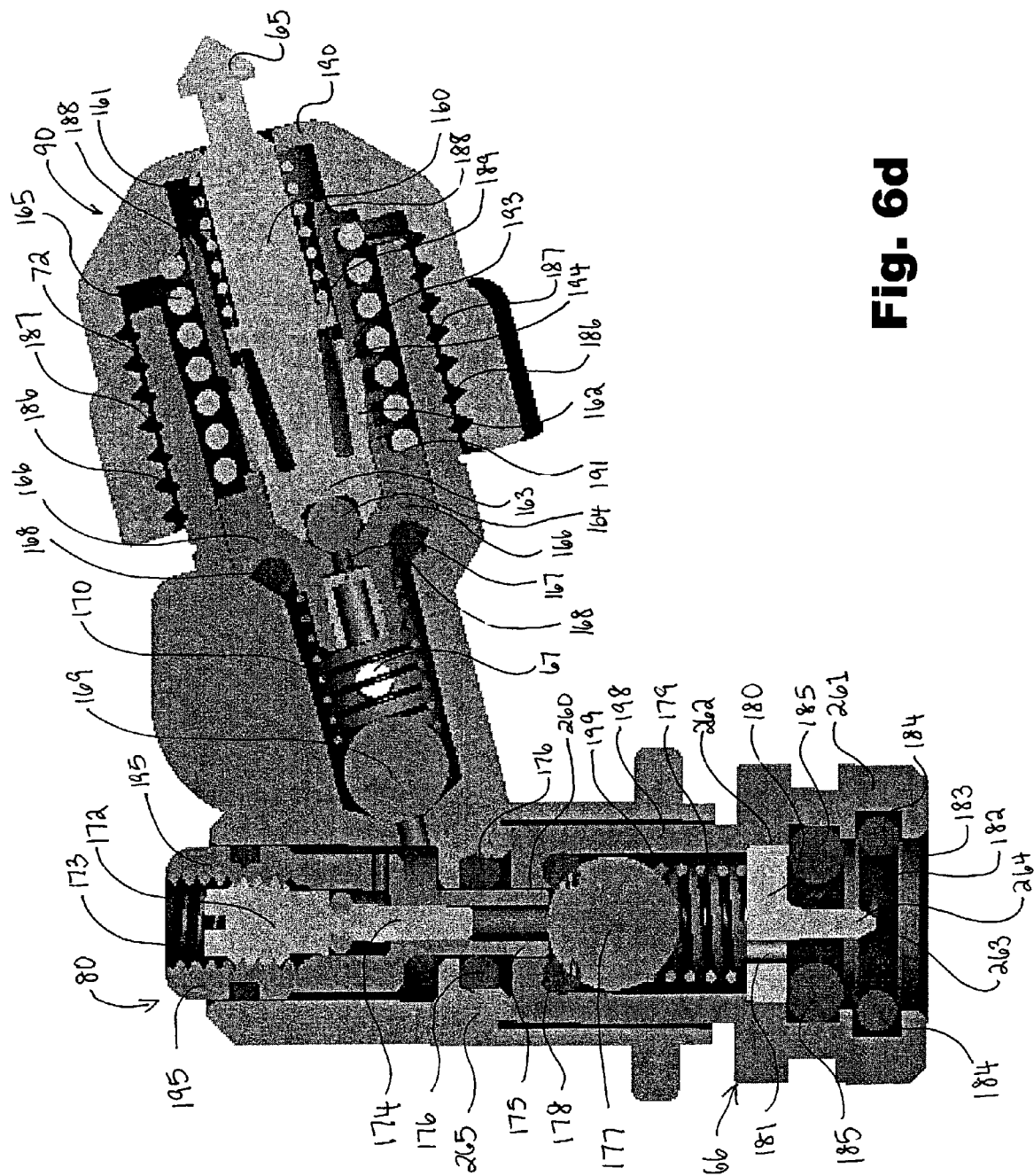
FIG. 6d is a cross-sectional view of the pneumatic valve of FIG. 6b.

An exemplary embodiment of the pneumatic valve base 71 is depicted in FIGS. 6b-6d. The base 71 includes a valve body 84 with a plurality of chambers within it. For example, the valve body 84 may define a fluid intake chamber 74 configured to be in fluid communication with a trigger interface chamber 75 through a trigger-controlled passage 85. The trigger interface chamber 75 is in fluid communication with a fluid transfer chamber 73 through an interchamber passage 81, and the fluid transfer chamber is in fluid communication with a relief cap interface chamber 76. The fluid connector 67 is in fluid communication with the fluid transfer chamber 73 and also with the hydraulic cylinder 102 through the hydraulic stem 103. The pneumatic valve 70 may additionally have an external opening 86 and fluid intake chamber 74 configured to connect to and form a fluid tight and/or hermetical seal with a gas cartridge interface 66, which in turn may be configured to connect to and form a fluid tight and/or hermetical seal with a gas cartridge 63. The gas cartridge 63 may also be a reservoir or fluid reservoir.

The fluid transfer chamber 73 may have a plurality of internal structures, for example, to facilitate interaction with the deflation valve portion 166 of the relief cap 90, and to also control fluid flow through the chamber 73 from the interchamber passage 81. For example, the fluid transfer chamber 73 may have lodged within it a fluid transfer ball 169 which, due to the force and contact from a fluid transfer spring 170, may be lodged in a chamfered portion of the fluid transfer chamber 73 that may block fluid communication through the interchamber passage 81. The end of the fluid transfer spring 170 opposite the fluid transfer ball 169 may be lodged, for example, up against a portion of the deflation valve 166 and may be disposed around a portion of the deflation valve 166.

The fluid intake chamber 74, trigger controlled passage 85, and trigger interface chamber 75 may additionally have a plurality of internal structural elements. For example, the fluid intake chamber 74 may have an external opening 86 on one end and a trigger controlled passage 85 on the other. The trigger controlled passage 85 may be configured to facilitate fluid communication between the fluid intake chamber 74 and a trigger interface chamber 75. The trigger interface chamber 75 may have on one end the trigger controlled passage 85 and on the other end a trigger opening 87. The trigger interface chamber 75 may be configured to receive a trigger interface 80.

In an exemplary embodiment, the trigger interface 80 may include trigger interface body 195 that is threaded on at least a part of its interior and has screwed within it a trigger interface plug 172. The trigger interface plug 172 may serve as an adjustable needle valve to regulate gas flow. The trigger interface body 195 may be configured to interface with, on one end, the trigger body 89 of the inflation trigger 61, and on the other end may have a trigger interface shaft 175 which may be hollow and have lodged within at least a part of the hollow portion a trigger plug shaft 174. The trigger interface plug 172 may be configured to have disposed around it an O-ring, for example, to maintain a fluid tight and/or hermetical seal between the trigger interface plug 172 and the inner portion of the trigger interface body 195. The trigger interface shaft 175 may be lodged in, for example, the trigger controlled passage 85 between the trigger interface chamber 75 and the fluid intake chamber 74. The trigger interface shaft 175 may have disposed around it a trigger controlled passage O-ring 176 which may be lodged in a O-ring receiver portion 196 of the trigger controlled passage 85. The trigger controlled passage O-ring 176 may, for example, provide at times a fluid tight and/or hermetical seal in the trigger controlled passage 85 between the valve body 84 and the trigger interface shaft 175, may ensure that the trigger interface shaft 185 is centered in the trigger controlled passage 85, and may also facilitate movement of the trigger interface shaft 175 relative to the valve body 84 and the trigger controlled passage 85. The trigger interface body 195 may also have disposed around it an trigger interface O-ring 171, for example, near the trigger opening 87 of the trigger interface chamber 75. The trigger interface O-ring 171 may facilitate a fluid tight and/or hermetical seal between the trigger interface body 195 and the valve body 84 around the trigger interface chamber 75, and may also facilitate movement of the trigger interface 80 relative to the valve body 84.

In another exemplary embodiment, the end of the trigger interface shaft 175 opposite the trigger interface body 195 may be in contact, through the insertion opening 260 of the gas cartridge interface 66, with a gas cartridge interface ball 177 lodged in the gas cartridge interface chamber 199 of the gas cartridge interface 66. The gas cartridge interface 66 may have an insertion portion 198 containing the gas cartridge interface ball 177. The gas cartridge interface ball 177 may be lodged up against a gas cartridge interface ball O-ring 178 which in turn may be disposed up against the insertion portion 198 around the insertion opening 260. The insertion portion 198 may be lodged in the fluid intake chamber 74 of the pneumatic base 71. A portion of the gas cartridge interface ball 177 may be lodged in the insertion opening 260 in addition to being in contact with the trigger interface shaft 175. On the side of the gas cartridge interface ball 177 opposite the insertion opening 260 may be a gas cartridge interface spring 179. The insertion portion 198 of the gas cartridge interface 66 may be lodged up against a portion of the valve body 84 disposed around the fluid intake chamber 74, and specifically may be lodged up against the wall portion 265 of the valve body 84 surrounding the trigger controlled passage 85. The interface between the insertion portion 198 of the gas cartridge interface 66 and the wall portion 265 may be fluid tight and/or hermetically sealed so as to prevent fluid flow from the chamber portion 199 of the gas cartridge interface 66 to the outside environment through, for example, the gap on the sides between the insertion portion 198 and the valve body 84 as depicted in FIG. 6d.

The gas cartridge interface spring 179 may, on the side opposite the gas cartridge interface ball 177, be up against a gas cartridge interface plug 180 which may be lodged in an interior opening 262 that roughly divides the gas interface cartridge 66 into the insertion portion 198 and interface portion 261. The gas cartridge interface plug 180 may have a gas cartridge interface plug passage 181 which may be configured to facilitate fluid communication between the insertion chamber 199 and the chamber portions 263 of the interface portion 261. The gas cartridge interface plug 180 may have a gas cartridge interface end 264 which may be in contact with a portion of the gas cartridge 63 that, if moved away from the chamber portion 199 of the insertion portion 198, would cause gas to flow from the gas cartridge 63 and into the gas cartridge interface 66. The gas cartridge interface 66 may also have a gas cartridge stopper O-ring 185 that may stop the gas cartridge 63 from being inserted further into the gas cartridge interface 66, and may also cushion the gas cartridge interface plug 180 so as to allow it to be retained substantially in the interior opening 262, even if it is moved slightly away from the chamber portion 199 of the insertion portion 198 due to pressure from the gas cartridge interface spring 179. The interface portion 261 may also have a gas cartridge receiver O-ring 184 lodged in gas cartridge receiver 182, for example, to grip the sides of a gas cartridge 63 and provide a fluid tight and/or hermetical seal between the gas cartridge 63 and the gas cartridge interface 66. The interface portion 261 of the gas cartridge interface may have portions to retain and hold the gas cartridge receiver O-ring 184 and the gas cartridge stopper O-ring 185.

The inflation trigger 61 may be connected to the pneumatic valve base 71 by a hinge interface 82 which may grip a hinge 68 disposed on the pneumatic valve base 71. The inflation trigger 61 may have a portion configured to interact with and/or seal a portion of the pneumatic valve 70, and additionally have a trigger interface 83 for actuation by the user.

At one end, the lever 64, as depicted in FIG. 6e, includes a lever connector receiver 291 configured to connect to the lever connector 32 of housing 20. At an opposite end, the lever 64 may also have a trigger connector receiver 92 configured to connect to a trigger connector 93 (see FIG. 1), which in turn may be connected to the inflation trigger 61. The lever body 94 may be configured to cover at least a portion of the gas cartridge 63 that may be lodged within the housing 20. The lever 64 may also be configured to be easily removable, for example, by disconnecting the trigger connector 93 from either the inflation trigger 61 or the lever 64, and then rotating the lever 64 away from the gas cartridge (using the lever connector 32 as the rotational axis), so that the gas cartridge 63 in the housing 20 is now accessible. In an exemplary embodiment, the gas cartridge may be accessible so as to facilitate disposal and/or replacement of the gas cartridge. Also in an exemplary embodiment, the gas cartridge 63 may be metal, contain $CO_2$ gas, weigh about 12 grams, and operate at an initial pressure of about 900 psi.

The pneumatic assembly 60 may have various alternate configurations. For example, with regards to the relief cap 90 screwed onto pneumatic base 71, any other fluid tight and/or hermetically sealed interface configuration that can withstand the stress from the internal gas pressure is also acceptable. In another example, various configurations other than the exemplary embodiment described above are contemplated that allow the pneumatic valve 70, when triggered, to flow gas from the gas cartridge interface 66 to the fluid connector 67. For example, the pneumatic valve 70 may only have one chamber and one seal, and triggering the pneumatic valve 70 may open that one seal. The relief cap 90, or other means for depressurizing the pneumatic valve, may also be connected to that one chamber. Other configurations are also contemplated that allow the pneumatic valve 70, when triggered, to stop the flow of gas from the gas cartridge interface 66 to the fluid connector 67. In another exemplary embodiment, the inflation trigger 61 may be a button, or any other type of interface where the user can manually actuate the fluid delivery system 10.

In various embodiments, the way in which in the depression or otherwise initiation of the inflation trigger 61 causes the actuation of components in the pneumatic assembly 60 may be varied. For example, the inflation trigger 61 may be mechanically coupled to the pneumatic assembly 60 through the trigger interface 80, and thus the force used to depress the inflation trigger 61 may physically move components of the pneumatic assembly 60. In another example, the inflation trigger 61 may be electrically coupled to the pneumatic assembly 60 through the trigger interface 80, and thus the force used to depress the inflation trigger 61 may not physically translate into movement of various components in the pneumatic assembly 60, but instead may send electronic signals to the pneumatic assembly which in turns may initiate a series of events that may cause the increase in gas pressure within at least parts of the pneumatic assembly 60 and/or hydraulic assembly 100.

It should be understood that with regard to the configuration of the pneumatic assembly 60, any configuration of the gas cartridge 63 and pneumatic assembly 60 that would facilitate fluid flow from the gas cartridge 63 to the pneumatic assembly 60 upon actuation of the inflation trigger 61 is acceptable. Additionally, any configuration that facilitates fluid flow from the pneumatic assembly 60 to the hydraulic assembly 100 is acceptable. Furthermore, any configuration that stops gas flow once the cease flow indication is given is acceptable. In addition, the various portions of the pneumatic assembly 60 may be spread out in various portions of the fluid delivery system 10, and may be connected by pneumatic lines.

In an exemplary embodiment shown in FIG. 1, the external interface 101 includes a strain relief portion that is integral with a balloon dilator 200 as the distal assembly. A catheter 201 extends from the strain relief portion and is in fluid communication with the external interface 101. Catheter 201 leads to a dilation balloon 202 at a distal end of the dilator 200. In an exemplary embodiment, the balloon dilator 200 may be fixedly connected to the external interface 101 during the manufacturing process. Accordingly, the fluid delivery system 10 may be sold with balloon dilator 200 already attached. This may be desirable if the fluid delivery system 10 is an inexpensive single use device that is disposable. In the case that the fluid delivery system 10 may be sold with the balloon dilator 200 attached via the balloon catheter 201, it may be preferable to have the balloon dilator 200 and balloon catheter 201 completely filled with fluid prior to use, for example, during the manufacturing process. This may be preferable because the presence of any air in the balloon dilator 200 or balloon catheter 201 may lead to inaccuracies in the system, as air is much more compliant than other fluids, that may be dangerous to the person. Alternatively, as described below, balloon dilator 200 may be sold separately and configured to be mated with the external interface 101. In addition, it may be preferable to provide the fluid delivery system 10 without fluid, and then fill the hydraulic assembly 100 with fluid at the time of operation to, for example, prevent leakage.

Commercially available balloon dilators that may be configured to be used in connection with the fluid delivery system 10 include CRE™ Wireguided Balloon Dilators and CRE™ Fixed Wire Balloon Dilators sold by Boston Scientific Corporation®. Such dilators include a balloon fixed to the end of a catheter and inflated by injecting through the catheter from a proximal fluid delivery device, for example, a fluid delivery system 10. The balloon is configured to be filled to three distinct diameters at three different fluid pressures. For example, if the pressure of the fluid in the balloon is about three atmospheres, then the balloon dilator diameter may be about 10 mm. In another example, if the pressure of the fluid in the balloon is about five atmospheres, then the balloon diameter may be about 11 mm. In yet another example, if the pressure of the fluid in the balloon is about eight atmospheres, then the balloon diameter may be about 12 mm. The CRE™ balloon dilators also may have rectilinear shoulders 203 on both ends joined by a central portion with a roughly uniform diameter along its length, have a high radial dilatation force 204 (i.e., is extremely hard when filled and may feel like an incompressible material such as metal or glass), and have an atraumatic tip 205 so as to reduce the trauma on the gastrointestinal tract during insertion.

In another embodiment, the balloon dilator 200 may have a sensor located on it, for example, in place of the atraumatic tip 205 as depicted in FIG. 1. The sensor may be configured to sense how the dilation is progressing, for example, whether the gastrointestinal stricture has been sufficiently dilated, and send data and/or results back to a portion of the fluid delivery system 10, for example, the electronic interface 40.

In alternative embodiments, the external interface 101 may be located on another portion of housing 20. In addition, the external interface 101 may connect or be configured to connect, for example, to other medical or non-medical devices or nothing at all, to emit a discharge of fluid from the fluid delivery system 10 for a variety of uses. The fluid delivery system 10 may include a universal connector to any one of a variety of distal devices for such uses. Examples of devices and uses in medical and non-medical applications include:

a device to perform stone lithotripsy, where the fluid delivery system may drive a hammer to crush stones that may be, for example, in the urinary tract;

a fastener/staple driver for driving fasteners/staples into tissue through the use of fluid pressure from the fluid delivery system, for use in arthroscopy or procedures to treat gastroesophageal reflux disease (GERD), such as fundoplication procedures, or full thickness reduction devices;

an outgassing packager where compressed gas may drive out sterilization gas present in a given packaging;

a drug injector either configured as an injection system driven by fluid pressure from the fluid delivery system, or configured to directly inject fluid containing the drugs from the fluid delivery system;

a device to perform power wash irrigation, for example, for washing out orifices, hemostatis (stopping bleeding), flushing out endoscopes, or non-medical applications;

a cutting nozzle that is configured to cut tissue or any other medical or non-medical substance, using the pressurized fluid from the fluid delivery system;

drills, brushes, scrapers, or other like devices for, for example, dental applications, or other non-medical applications;

a cast immobilizer configured to be inflated by the fluid from the fluid delivery system, for example, to treat broken bones, fractured bones, and muscle tears, or other non-medical applications;

an organ distender, for example, to test tissue strength.

a suction device configured to operate, for example, by connecting the external interface to the suction device to create suction, or by preinflating the system and then deflating the system while it is deployed at the desired location;

a biopsy device, for example, a clamping jaw, where the fluid delivery system may be used to actuate the jaw so as to remove a small sample of tissue for examination.

aspirators, for example, a transbronchial needle aspirator;

clamps, where the fluid pressure from the fluid delivery system may be used to close and/or advance the clamps, for example, in a biopsy procedure, or other non-medical applications;

a viscous material deliverer, which may just be a tube, where the fluid itself may actually constitute a contrast, such as renografin, or fillers, for example, for arthroscopy or to fill abdominal or cranial aneurysms, or other non-medical applications;

a power mixer to mix viscous agents such as fibrin glues, enteryz, adhesives, epoxies, or other items that may be used for occlusions, fractures, or as a sealant, or other non-medical applications;

a steerable catheter tip that responds to changes in fluid pressure;

a catheter tube that when fluid is applied to it may stiffen, for example, during the therapy portion of a biopsy procedure, or other non-medical applications;

a device that heats and/or cools the fluid, so as to deliver heated and/or cooled fluid to tissue, for example, to treat ablations, polyps, or warts, or other non-medical applications;

a harmonic scalpel or other device where, for example, the change in fluid pressure causes the scalpel to vibrate;

a device that causes a water surge, for example, to move organs or create downward pressure in the gastrointestinal tract as an anti-reflux action, or other non-medical applications;

a general actuator that actuates, for example, surgical instruments, or other non-medical applications;

a catheter that, based on the fluid pressure, creates vibrations at ultrasonic frequencies, for example, for diagnostics, therapeutics, ablations, and cutting, or other non-medical applications;

an expandable brace that may be inflated, for example, to promote bone growth, or other non-medical applications;
a catheter that may bend based on changes in fluid pressure;
a pressure cuff that may be inflated and deflated around parts of the body, for example, to measure blood pressure or stimulate blood flow, or other non-medical applications;
a stent deployer where the control of the fluid pressure may allow the controlled deployment of the stent in the desired bodily location, or other non-medical applications;
a tissue insufflator that may deploy gas or powder into a body cavity, for example, during laparoscopic surgery;
a trocar that may draw off fluids from a body cavity;
a rotational snare that uses fluid pressure to drive and/or spin the snare;
a telescoping guidewire that may use fluid pressure to advance movement of the distal end of the guidewires, for example, through difficult lesions, or other non-medical applications;
a drug pack, where the drug packs is loaded into a housing and then may be compressed by the fluid when delivery is desired, or other non-medical applications;
a drug pump, where the fluid pressure may drive a temporary or permanent drug pump to infuse drugs into the body, or other non-medical applications;
a needle driver which may assist in pushing needles into, for example, hard lesion or bones, or other non-medical applications;
a device that may control the delivery of ligation bands, for example, around a blood vessel to stop it from bleeding or another structure to constrict it;
inflatable bolsters on PEG tubes;
inflatable anchors on various catheters;
a bougie used to enlarge strictures and powered by the fluid pressure to inflate and/or deflate to multiple sizes;
a cystic fibrosis impactor powered by compressed fluid that may be used to provide force to the lungs;
an inflatable stent that could have a low profile delivery but able to be rigidly deployed;
a power mechanical dilator for extending, for example, a mesh or a linkage within the body, or other non-medical applications;
a device for delivering bulking agents such as enteryx for GERD treatment and collagens;
an intra-aortic balloon pump that may be relatively small because a compressor may no longer be necessary;
an intravenous bag so as to replace and/or improve on the gravity driven intravenous bag by controlling fluid output;
a catheter to serve as a portable catheter leak test;
a device which may use compressed gas to drive undesired gas out of a given environment;
an injector to control the injection of a substance into a desired location;
a power wash irrigator to washout a desired device or location;
a balloon inflation device;
a toy projectile so as to use the fluid pressure to propel the toy projectile, such as a nerf ball, other toy balls, or toy discs;
a water gun;
a tattoo needle where the fluid pressure drives the needle and the colors may be selected from a color wheel;
a rotator where the fluid pressure drives the rotation of the rotator;
a power mechanical dilator for extending, for example, a mesh or a linkage;
an inflator to inflate toys.
construction applications requiring a high pressure fluid jet (i.e. cutters); or
toys such as water guns;

In adapting the fluid delivery system 10 for use with systems in, for example, the medical and non-medical applications described above, portions of the fluid delivery system 10 may need to be reconfigured or adapted in order to meet the requirements of the medical and/or non-medical applications and/or uses.

In an exemplary embodiment, the hydraulic assembly 100 and/or pneumatic assembly 60 may be configured to have an exterior double seal system around the hydraulic assembly 100 and/or pneumatic assembly 60 so as to provide a backup system for preventing leakage from either assembly. The entire fluid delivery system 10, or at least its sensitive portions, are preferably hermetically sealed so as to avoid mold, bacteria, and dirt.

In an embodiment, the fluid delivery system 10 may be a single use system that may be disposed of after a single use. In another embodiment, the fluid delivery system 10 may be a portable home kit that is configured to allow self-dilatation. In yet another exemplary embodiment, the fluid delivery system 10 may be reusable. According to that embodiment, at least components or portions of the fluid delivery system 10 may be disposable and/or replaceable, for example, as the life of the component runs out or to maintain sterility in the case of components that contact a patient. For example, the hydraulic assembly 100, or at least its fluid containing portion, may be configured to be removed from within the housing 20 of the fluid delivery system 10 and replaced. In another example, the gas cartridge 63 may be configured to be removed and replaced. In yet another example, the battery from the electronic interface 40 may be configured to be removed and replaced. The electronic interface and circuitry may be configured to indicate to a user that a component may be in need of replacement.

As a further example, the external interface 101 may be configured to selectively attach to any number of distal components through any suitable attachment mechanism known in the art. Such distal components, such as balloon dilator 200 or any other medical or non-medical device, may be sold separately and have universal, standard attachment means at its proximal end to attach to the external interface 101 of the fluid delivery system 10 prior to use. After use, the distal component may be replaced/disposed, with the fluid delivery system 10 being reusable.

In various embodiments, many of the parts in the fluid delivery system 10 may be injection molded, for example, with plastic or other suitable material. The components, however, may be made of other materials using a variety of other methods, for example, machining or casting metal. In addition, certain parts are preferably made of biocompatible materials, including those parts in contact with a patient. In another example, the materials of the fluid delivery system 10 and/or the packaging used to ship the fluid delivery system 10 may be made of environmentally friendly materials. The system 10 is preferably made out of material that do not corrode or deteriorate during shelf life, preferably do not leak fluids during shelf life, preferably is made out of materials that can perform after shelf life, and preferably withstand sterility concerns.

In yet another embodiment, the fluid delivery system 10 may be configured as a dual action system. For example, the fluid delivery system 10 may be configured to have two external interfaces 101 configured to connect to two different external devices, for example, two different balloon catheters or two balloons of the same catheter with each balloon having a separate inflation lumen. These external interfaces may be separately controlled by separate elements on the fluid delivery system 10, for example, separate triggers actuating separate pneumatic assemblies 60 and/or hydraulic assemblies 100 connected to separate external interfaces. However, the external interfaces may also be controlled by the same elements on the fluid delivery system 10, for example, the same trigger actuating the same pneumatic assembly 60 and/or hydraulic assembly 100 connected to the separate external interfaces. In such a fluid delivery system 10, the external interfaces may work in conjunction, meaning that both external interfaces may dispense fluid simultaneously in the same amount. However, in another example, the fluid delivery system 10 may be configured so that even though the external interfaces are controlled by the same components, the user has the option of dispensing fluid from only one of the external interfaces and not the other.

In still another embodiment, the fluid delivery system 10 may be configured as multiple function system. For example, the fluid delivery system 10 may have multiple valves, multiple ports, and multiple actuators to perform multiple functions. In an example of such a device, a user may actuate a button to fill a balloon catheter attached to an external interface of the fluid delivery system 10, but then may actuate another trigger to actuate some other medical function, for example, a drill. In this way, the dispensation of fluid may be just one of many functions of the fluid delivery system 10.

In another exemplary embodiment, the gas cartridge 63 may actually be a gas system that can provide gas pressure to the pneumatic assembly without necessarily requiring an internal gas cartridge 63. For example, the gas system may be a compressed gas reservoir located in a hospital, a small onboard compressor, a gas cartridge loaded on a separate device, or a hand pump.

In another exemplary embodiment, the fluid delivery system 10 may glow in the dark or may have appropriate buttons and lights for enabling the device to light up. This may be desirable as many laboratories are often kept in dark conditions.

In an exemplary embodiment, the entire fluid delivery system 10, or just portions of the fluid delivery system 10, may be automated and controlled with various feedback loops and/or software.

In a further embodiment, the fluid delivery system 10 may use other sources of power, for example, power sources already present in the setting that the devices is used, for example, a hospital. In such a case, the device may include suitable power source connectors for connection to the power source.

The fluid delivery system 10 described and depicted in connection with FIGS. 1-6d is an exemplary embodiment. Other combinations of parts and components are contemplated, such as those depicted in FIGS. 7a-7f.

Figure 7A:
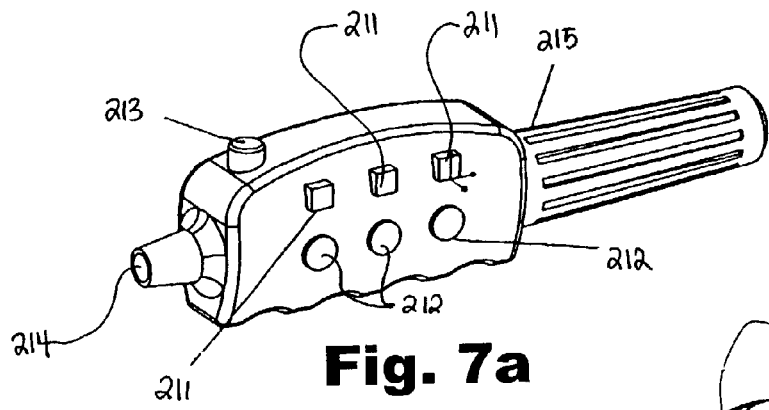
FIG. 7a is a perspective view of a fluid delivery system having a sword-like configuration, according to an embodiment of the present invention.

For example, the fluid delivery system 10 may be in the shape of a sword-like handle, as depicted in FIG. 7a, where a handle grip portion 210 contains both the pneumatic assembly and the hydraulic assembly, and the electronic interface portions, for instance the indicators 211 and buttons 212 that function similar to their counterparts depicted in FIGS. 6a-6d, may be disposed on various parts of the handle grip portion 210. It is also contemplated, however that the buttons 212 may function as deflation buttons which may, when depressed, automatically decrease the pressure in the hydraulic assembly to one or more predetermined amounts. In this exemplary embodiment, the external interface 214 may be located where the shaft of the sword would leave the handle portion 210, the inflation trigger 213 may be located on the top of the handle portion 210, and the gas cartridge 215 may be located on the back of the handle portion 210.

Figure 7B:
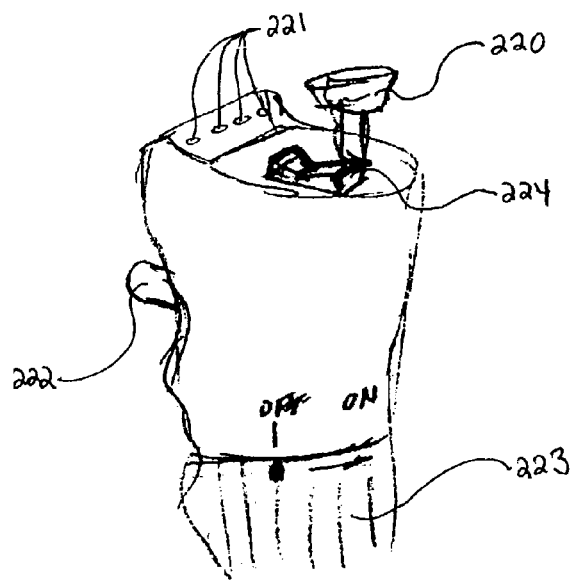
FIG. 7b is a perspective view of another fluid delivery system having a joystick-type configuration, according to an embodiment of the present invention.

In another exemplary embodiment, the fluid delivery system 10 may be configured in a joystick-like shape, similar to a video game joystick, as depicted in FIG. 7b. In this embodiment, movement of the joystick 220 would act to increase and/or decrease the pressure in the fluid delivery system. The indicators 221 and button 224, which function similar to their counterparts depicted in FIGS. 6a-6d, may be on top of the device next to the joystick 220, the rapid deflation button 222 may be on the front of the device, and the entire device may be powered on by twisting an auxiliary portion 223 of the device or flipping a switch on auxiliary portion 223.

Figure 7D:
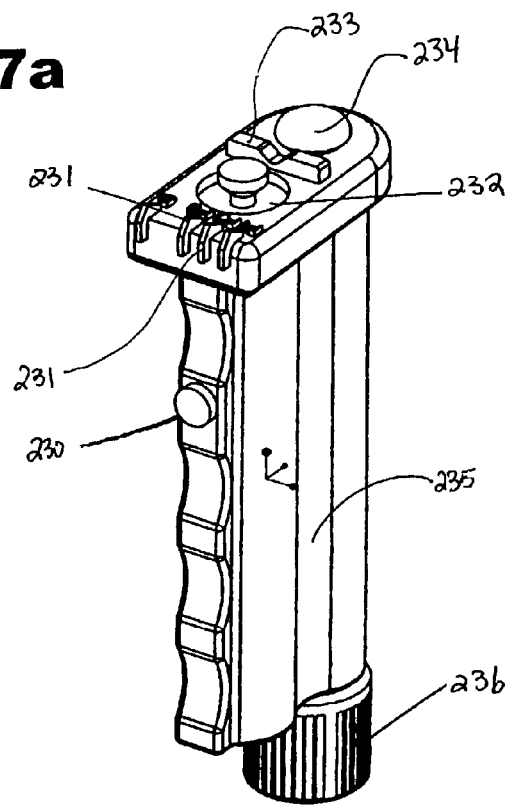
FIG. 7d is a perspective view of another fluid delivery system having a different joystick-type configuration, according to an embodiment of the present invention.
Figure 7C:
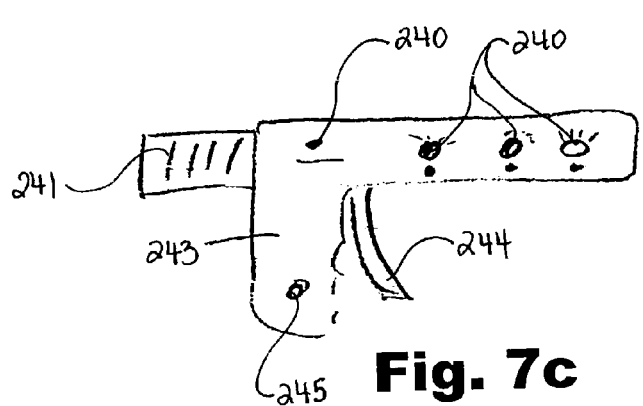
FIG. 7c is a perspective view of yet another fluid delivery system having a gun-like configuration, according to an embodiment of the present invention.

In yet another exemplary embodiment, the fluid delivery system 10 may have a gun-style shape as depicted in FIG. 7c. This embodiment is similar to the exemplary embodiment depicted in FIGS. 1-6e, as it may have a handle portion 243 with a trigger 244 located forward of the handle portion 243. However, the indicators 240, which function similar to their counterparts depicted in FIGS. 6a-6d, may be on the side of the device, the deflation button 245 may be on the handle portion 243, and the gas cartridge 241 may protrude out of the proximal end 242 of the device.

In still another exemplary embodiment, the fluid delivery system 10 may be configured in a joystick-like shape, similar to that used for control of an airplane, as depicted in FIG. 7d. Some features of this embodiment may include a joystick 232 which may control the increase and/or decrease of pressure in the device, rapid deflation button 230 on a finger accommodating portion 237 of the joystick handle 235, actuation by twisting a bottom portion 236 of the device around its central axis, a replaceable hydraulic assembly through a top cartridge 234 of the device, and indicators 231 and an electronic interface button 233, which function similar to their counterparts depicted in FIGS. 6a-6d, also located on the top of the device.

Figure 7E:
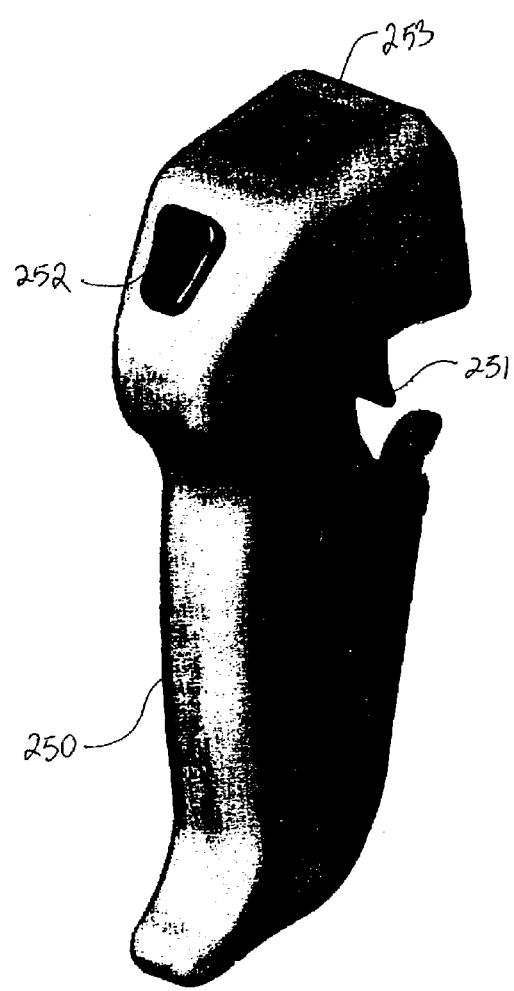
FIGS. 7e-f are perspective views of additional fluid delivery systems, according to various embodiments of the present invention.
Figure 7F:
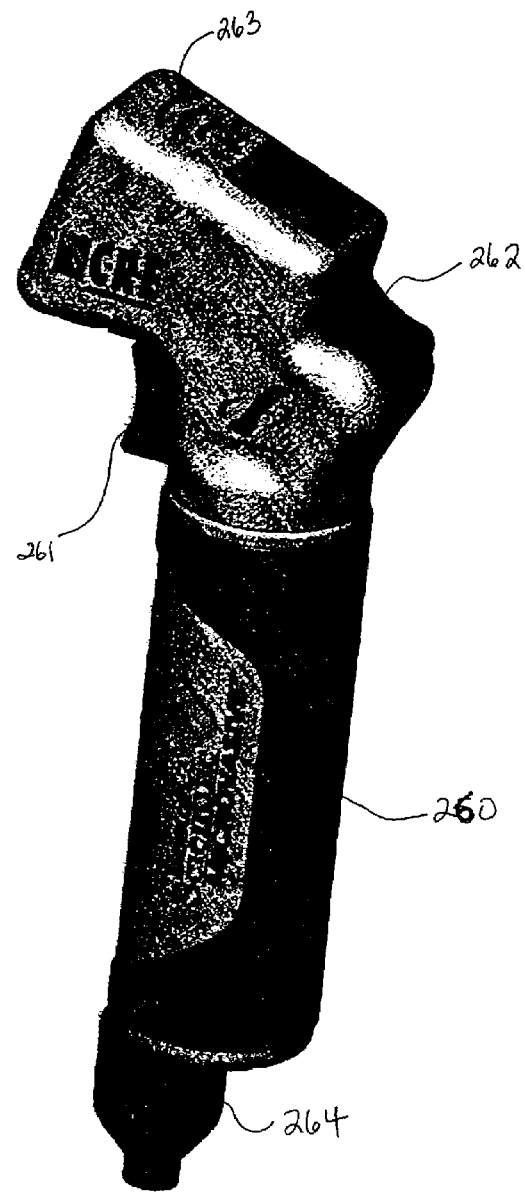

In other exemplary embodiments, FIGS. 7e-7f depict aesthetically different exemplary embodiments of the fluid delivery system. The exemplary embodiments may include handle portions 250, 260 with inflation triggers 251, 261 on one side and deflation buttons 252, 262 on the other. The exemplary embodiments may also have indicators 253, 263 located on top of the handle portions 250, 260. In addition, one of the exemplary embodiments may be powered on by twisting a bottom portion 264 about its central axis.

An exemplary method of using the embodiment of the fluid delivery system depicted in FIGS. 1-6d will now be described. As an initial step, the user must access the treatment site in a patient through any suitable method known in the art. For example, the embodiment shown in these Figures may be used in an endoscopic procedure that uses an endoscope to gain access to a treatment site, such as a stricture within an esophagus. According to that method, the user may use any suitable endoscope having a lumen that may accommodate the balloon dilator 200 when balloon 202 is in an uninflated state. Once the user accesses the treatment site with the endoscope through a conventional method, the user may advance balloon dilator 200 through the lumen until it exits the distal end of the endoscope lumen at the treatment site. Any suitable, known methods of visualizing the site during the procedure any be used, including imaging techniques.

Once balloon 202 is properly positioned at the treatment site, the user may depress the trigger interface 83 of the inflation trigger 61 to initiate inflation of balloon 202. To continue inflation of the balloon 202, the user may thereafter release the trigger interface 83 of the trigger and allow the fluid delivery system to automatically inflate the balloon 202, or the user may continue to hold down the trigger interface 83 of the inflation trigger 61 to continue inflation of the balloon 202.

Depressing the inflation trigger 61 may cause the trigger interface 80 to move toward the trigger controlled passage 85 and the gas cartridge interface 66, and in particular may cause the trigger interface shaft 175 to move deeper into the insertion portion 198 of the gas trigger interface 66 through the insertion opening 260. This movement of the trigger interface shaft 175 may move gas cartridge interface ball 177 away from the insertion opening 260 of the insertion portion 198, and may unseal the insertion opening 260 to allow fluid communication from the chamber portion 199 of the insertion portion 198, through the insertion opening 260, through the trigger controlled passage 85 and into the trigger interface chamber 75. Some fluid may try to flow into the hollow portion of the trigger interface shaft 175, but it may be blocked, for example, by the trigger plug shaft 174 of the trigger interface plug 172.

The movement of the gas cartridge interface ball 177 away from the insertion opening 260 on the gas cartridge interface 66 may in turn cause the gas cartridge interface spring 179 to compress. The compression of the gas cartridge interface spring 179 may in turn cause the movement of the gas cartridge interface plug 180 away from insertion portion 198 of the gas cartridge interface 66 and cause some compression of the gas cartridge stopper O-ring 185 either between the gas cartridge interface plug 180 and the gas cartridge 63, or between the gas cartridge interface plug 180 and the wall of the interface portion 261 of the gas cartridge interface 66. The movement of the gas cartridge interface plug 180 away from insertion portion 198 of the gas cartridge interface 66 may also cause the cartridge interface end 264 to move away from the interior opening 262 and come into contact with a portion of the gas cartridge 63. The contact may cause fluid to flow, for example, from the gas cartridge 63, through at least a portion of the gas cartridge receiver 182 on the interface portion 261 of the gas cartridge interface 66, into the gas cartridge interface plug passage 181 disposed in the gas cartridge interface plug 180 and into the chamber portion 199 of the insertion portion 198 of the gas interface cartridge 66. The gas cartridge receiver O-ring 184 and the gas cartridge stopper O-ring 185 may be configured to prevent fluid from flowing out of the interface portion 261 and into the external environment.

Once the fluid flows from the gas cartridge 63, through the interface portion 261 and insertion portion 198 of the gas cartridge interface 66, through the insertion opening 260, the fluid intake chamber 74, and the trigger controlled passage 85 into the trigger interface chamber 75, the fluid may flow through the interchamber passage 81 and into at least a portion of the fluid transfer chamber 73. Initially, the fluid may not flow well through the interchamber passage 81 because the fluid transfer ball 169 is lodged and covering the opening of the interchamber passage 81 in the fluid transfer chamber 73. However, enough fluid pressure may build up in, for example, the trigger interface chamber 75 that the fluid transfer ball 169 may be forced by the buildup in pressure in the trigger interface chamber 75 to move away from the interchamber passage 81 and allow fluid flow into the fluid transfer chamber 73. From the fluid transfer chamber 73, the gas may flow through the fluid connector 67 into a portion of the hydraulic assembly 100. In an exemplary embodiment, although some fluid may flow into the deflation valve passage 167 and attempt to flow into the relief cap interface chamber 76, it may be blocked by the deflation ball 166 lodged in the opening of the deflation valve passage 167.

The gas may flow from the fluid connector 67 into the hydraulic stem 110 of the hydraulic assembly 100. The gas then flows in the hydraulic stem 110 from the pneumatic interface 119, through the shaft 118, and out the hydraulic cylinder interface 120 into the hydraulic cylinder 102. More particularly, the gas flows from the hydraulic cylinder interface 120 of the hydraulic stem 110 into the hydraulic stem interface 121 of the hydraulic cylinder 102, and into at least a portion of the fluid chamber 127 of the hydraulic cylinder 102. Once inside the fluid chamber 127, the gas contacts at least a portion of the proximal wall 134 of the primary piston 105, which initially may be in contact with or at least adjacent to the proximal wall 122 of the hydraulic cylinder 102. As the sidewall 133 of the primary piston 105 and the inner surface 125 of the sidewall 124 of the hydraulic cylinder 102 may form, with or without the assistance of a primary piston O-ring 112, a fluid tight and/or hermetical seal, the introduction and/or accumulation of gas into the fluid chamber 127 places pressure on several walls and, in particular, the proximal wall 134 of the primary piston 105.

As this pressure builds on the proximal wall 134 of the primary piston 105, in this exemplary embodiment, the primary piston 105 may begin to move away from the proximal wall 122 of the hydraulic cylinder 102. As the primary piston 105 moves, it may compress primary piston spring 113. As described above, the primary piston spring 113 contacts on one end a spring receiver 130 on the primary piston 105, and on the other end the proximal wall 156 of the central portion 154 of the hydraulic cap 104. As the primary piston 105 moves away from the proximal wall 122 of the hydraulic cylinder, the hydraulic cap 104 may remain stationary, for example, because it is locked relative to the hydraulic cylinder 102. Thus, the primary piston spring 113 compresses between the primary piston 105 and the hydraulic cap 104.

The movement of the primary piston 105 may also cause the flow of fluid which may be present in the portion of the fluid chamber 127 bounded by the primary piston 105, sidewall 124 of the hydraulic cylinder 102, and the proximal portions (proximal end 140, proximal sidewall 142, proximal wall 148) of the hydraulic cap 104. The fluid may comprise any liquid or other material capable of filling a balloon dilator 200, for example, water, saline, propylene glycol, or mineral oil. In various embodiments, the fluid may flow in a plurality of ways and/or to a plurality of places, for example, out of the fluid chamber 127. However, any configuration that, due to the increases in gas pressure, increases the volume of the fluid chamber 127 bounded by the primary piston 105, sidewall 124 of the hydraulic cylinder 102, and the proximal portions (proximal end 140, proximal sidewall 142, proximal wall 148) of the hydraulic cap 104 is acceptable.

In this exemplary embodiment, one place the fluid may flow is through the proximal opening 148 of the external interface connector 147, through the external interface connector 147, and out the distal opening 149 of the external interface connector 147. From there, the fluid may flow directly into external interface 101 or through at least one luer hub 108 into external interface 101. Alternatively, the external interface connector 147 may be the external interface 101. The fluid then flows out of the fluid delivery system 10 and into, for example, catheter 201 of balloon dilator 200 to inflate balloon 202.

Another place the fluid may flow is through the proximal opening 141 of the proximal end 140 of the hydraulic cap 104 into the inner chamber 153 of the hydraulic cap 104. There, the fluid may come into contact with at least a portion of the proximal wall 161 of the expansion piston 106. Accordingly, as the sidewall 162 of the expansion piston 106 and the inner surface 150 of proximal sidewall 142 of the hydraulic cap 104 may form a fluid tight and/or hermetical seal, with or without the assistance of an expansion piston O-ring disposed between the sidewalls 142, 162, fluid pressure may build against the proximal wall 161 of the expansion piston 106. As this pressure builds, the expansion piston 106 may move away from the proximal end 140 of the hydraulic cap 104 and toward the distal protrusions 143 of the hydraulic cap 104. In doing so, the expansion piston 106, which may be connected to or at least be in contact with an expansion spring 114, may cause the expansion spring 114 to compress between, for example, the spring receiver 165 of the expansion piston 116 and the spring retainer 107. The spring retainer 107 may be connected to a portion of the housing 20, for example, beneath the external surface notch 23, and between the structural support 33 and connector 27a in the distal portion of the housing 20, and may not move relative to the housing 20.

In an exemplary embodiment, it is contemplated that the expansion piston 106, expansion spring 114, and hydraulic cap 104 assembly may be configured so that the expansion piston does not move completely past the central portion 154 of the hydraulic cap 104 and into the portion of the inner chamber 153 between the distal protrusions. This may be to prevent a fluid seal from being broken in the hydraulic assembly 100. For example, the assembly could be designed such that the maximum compression of the expansion spring 114 does not allow the expansion piston 106 to move past a certain point distally, or that the expansion piston 106 may have a distal opening 167 leading to an inner chamber 163 with a chamfered proximal end 166 in the proximal wall 161 configured to receive the proximal end of the spring retainer 107, and thus limit the distal movement of the expansion piston 106. However, any energy storage system that stores energy due to changes in fluid pressure, for example, in the hydraulic assembly is acceptable.

Fluid also may flow into the proximal opening 145 of the check valve connector 144, through the check valve connector 144, through the distal opening 146 of the check valve connector 144, and into at least a portion of the check valve 115 through, for example, the hydraulic cap interface 175. In another exemplary embodiment, the fluid may already be present in at least a portion of the check valve 115. Initially, the check valve 115 may be configured to prevent fluid flow out of the check valve 115, despite building fluid pressure due to the fluid flow in other parts of the hydraulic assembly 100. For example, the interior of the check valve 115 may be configured to prevent fluid flow, or the valve cap 180 may be configured to prevent fluid flow.

Fluid also may flow through the pressure sensor port 152 of the hydraulic cap 104 and into a portion of the pressure sensor subassembly 116, for example, the fluid intake opening 187 of the hydraulic cap interface 185. However, the pressure sensor subassembly may not have a fluid intake opening 187, and instead may take pressure or other measurements on an exterior surface. In another exemplary embodiment, the fluid may already be present in at least a portion of the pressure sensor subassembly 116. The electronic housing 186 of the pressure sensor subassembly 116 may have electronics, circuits, or other means configured to measure pressure, or take other readings, from the fluid. The pressure sensor subassembly 116 may continuously take such fluid readings, or periodically take them.

In an exemplary embodiment, the electronic housing 186 of the pressure sensor subassembly 116 may transmit a signal, for example, the pressure readings, from the pressure sensor subassembly 116 to the electronic interface 40. These signals may be transmitted by wire, radio waves, or any other suitable hods. The signals may be received in the electronic interface 40 by the pressure sensor header connector 44, which may be disposed on the electronic interface board 54. From there, the electronic interface 40 may house electronic components within the electronic interface housing 53 to convert the signals and display them on the display 41. For example, the display 41 may show a timer, pressure readings, size readings (for example, for a balloon dilator), or any other type of relevant information, including having indicators that show the same reading as the other indicators 49, 50.

The electronic interface 40 may also have indicators 49, 50 which indicate, for example, when the pressure readings from the pressure sensor subassembly 116 reach certain thresholds (for example, indicators 49a), or indicate whether the pressure in the hydraulic assembly 100 is increasing or decreasing (for example, indicators 49b). For example, in the case of balloon dilators, specific pressure measurements may indicate specific desired balloon sizes. Using this information, a user may, for example, release the inflation trigger 61 and prevent further fluid flow in the hydraulic assembly 100 when the electronic interface 40 indicates that the balloon has reached a certain size, or the electronic interface 40, without the input of the user, may automatically send a signal to either the hydraulic assembly 100 or the pneumatic assembly 60 to automatically stop the fluid flow when it receives measurements that indicate the balloon has reached a certain size. Once again, the use of balloon sizes in conjunction with indicators is exemplary, and any similar measurements that require such indications is also contemplated.

The electronic interface 40 may, when certain readings are received from the pressure sensor subassembly 116 and/or processed, emit a sound, for example, from the audio beeper 48. In one exemplary embodiment, the sound from the audio beeper 48 could coincide with the indication from the indicator 49, 50. The user may heed these indications and, for example, release the inflation trigger 61 to halt the increase of gas pressure within the pneumatic assembly 60. The electronic interface may also have a mute button to allow the user to silence the audio beeper 48.

The electronic interface 40 may also have an indicator that indicates there is an error in the system, for example, indicator 49c. Some errors may be, for example, the system is overloading, there is no power, or the electronic interface 40 is not receiving any signals. If the user sees this error indicator 49c or other indicators 49, 50, the user may, for example, press the deflation button 62 and cause the depressurization of the pneumatic assembly 60, or initiate the rapid depressurization valve and cause the rapid equalization of gas pressure between the gas chamber portions of the pneumatic assembly 60 and the outside environment. In another embodiment, the depressurization of the pneumatic assembly 60 may be automatic, and not require any input from the user.

Once the fluid delivery system 10 is given an indication that fluid flow is to cease, the following may occur. The indication may be a manual indication done by the user, for example, by releasing the trigger interface 83 of the inflation trigger 61, or an automatic indication done by the electronic interface 40, for example, when the pressure and/or size measurements reach a predetermined level. In an exemplary embodiment, once the fluid delivery system 10 receives the indication to cease gas flow, the pneumatic valve may be configured to stop gas flow within, for example, 500 ms. In another example, the indication to cease gas flow may be that the gas pressure in the pneumatic valve 70 reaches a predetermined maximum value, in which case the high pressure valves 91 on the relief cap 90 may be configured to automatically release gas out of the chambers in the pneumatic valve 70. This may be done whether or not the user has given the manual indication to stop, for example, by releasing the inflation trigger 61.

In one exemplary embodiment, a valve spring may be located in the trigger interface chamber 75, and be connected to, or at least in contact with, on one side by a portion of the inflation trigger 61, and on the other side by a portion of the valve body 84 of the pneumatic valve 70. Accordingly, when the user releases the trigger interface 83 of the inflation trigger 61, the valve spring may cause the inflation trigger 61 to pivot away from the pneumatic valve 70, the hinge 68 possibly being the rotational axis of the inflation trigger 61. When this occurs, the inflation trigger 61 may at least partially cause the trigger interface 80 to move away from the gas cartridge interface 66 and the trigger controlled passage 85, and toward and/or further through the trigger opening 87. The movement of the trigger interface 80 may also be assisted by the expansion of the gas cartridge interface spring 179, as the expansion of the gas cartridge interface spring 179 may cause the gas cartridge interface ball 177 to move toward the insertion opening 260 of the insertion portion 198 and become lodged in the insertion opening 260 and against the gas cartridge interface ball O-ring 178. The movement and lodging of the gas cartridge interface ball 177 may cause the trigger interface shaft 175 to move away from the insertion portion 198 of the gas cartridge interface 66, thus further facilitating movement of the trigger interface 80. Accordingly, the gas cartridge interface plug 180, due to the fact that it now has less pressure on it, for example, from the gas cartridge interface spring 179, may again become completely lodged in the interior opening 262 of the gas cartridge interface 66.

The movement of the aforementioned elements may cause fluid communication to be cut off in several ways. For example, fluid communication between the gas cartridge 63 and the gas cartridge receiver 182 on the interface portion 261 may be cut off due to the cartridge interface end 264 no longer causing fluid to flow from the gas cartridge 63. In another example, fluid communication between the chamber portion 199 of the insertion portion 198 of the gas cartridge interface 66 and the trigger interface chamber 75 through the trigger controlled passage 85 and insertion opening 260 may be cut off due to the gas cartridge interface ball 177 being lodged in the insertion opening 260. In yet another example, fluid communication between the trigger interface chamber 75 and the fluid transfer chamber 73 through the interchamber passage 81 may be cut off due to the fluid transfer ball 169 being lodged in the portion of the fluid transfer chamber 73 abutting the interchamber passage 81. The lodging of the fluid transfer ball 169 may occur because the fluid pressure from the trigger interface chamber 75 may no longer be as great as the expansion pressure from the fluid transfer spring 170.

Thus, because at least of the above elements may prevent further fluid flow through the pneumatic valve 70, the fluid may stop flowing from the fluid transfer chamber 73, through the fluid connector 67 and hydraulic stem 103 into the hydraulic cylinder 102. This stop in gas flow may stop the movement of the primary piston 105 away from the proximal wall 122 of the hydraulic cylinder 102, and thus may stop the fluid flow from the hydraulic cylinder 102 into various portions of the hydraulic cap 104, for example, the inner chamber 153 of the hydraulic cap 104, the check valve connector 144, the pressure sensor port 152, and the external interface connector 147.

In various embodiments, the user, once the gas flow to the pneumatic assembly 60 and/or fluid pressure buildup in the hydraulic assembly 100 has stopped, may reinitiate the process of increasing the gas pressure and/or fluid pressure in the pneumatic assembly 60 and/or hydraulic assembly 100 by, for example, again depressing the inflation trigger 61. This may be desirable, for example, to increase the size of the balloon dilator 200 to the next desired size. Accordingly, the entire above described fluid flow method may be repeated.

In an exemplary embodiment, the user may deflate the fluid delivery system 10. In an exemplary embodiment, once the deflation signal is given, the fluid delivery system 10 may be configured to deflate a balloon dilator 200 and/or take in fluids from the external interface 101 for an amount of time, for example, about 20-30 seconds. For example, the user may trigger the deflation button 62, which may cause the deflation interface 65 on the relief cap 90 to move the deflation shaft 160 and the deflation ball interface 163 toward the proximal end 190 of the relief cap 90. The movement of the deflation shaft 161 may cause the deflation spring 161 to compress between the deflation spring receiver 189 and the portion of the relief cap 90 surrounding the proximal end 190. The movement of the deflation ball interface 163 may cause the deflation ball 164, previously lodged in and preventing fluid communication through the deflation valve passage 167, to become unsealed and allow fluid communication between the fluid transfer chamber 73 and the portion of the relief cap interface chamber 76 between the deflation valve legs 188. The deflation valve shaft receivers 193 on the deflation valve legs 188 may prevent movement of the deflation shaft and 160 and deflation ball interface 163 too far towards the proximal end 190 of the relief cap 90 by virtue of them butting up against the deflation leg receivers 194 on the deflation shaft positioners 162.

Due to the movement of the deflation ball interface 163, and consequently the deflation ball 166 away from the deflation valve passage 167, fluid may flow from the fluid transfer chamber 73, through the deflation valve passage 167, through the gap between the deflation valve 166 and the deflation ball interface 163, into the relief cap interface chamber 76, and then out into the external environment. The flow of fluid out into the external environment may be, for example, through the opening in the proximal end 190 of the relief cap 90 where the deflation interface 65 is located, or through the gap between the grooved portion 72 on the valve body 84 and the grooved portion 186 on the relief cap 90. Accordingly, at least some the pressurized gas may flow and/or escape from the pressurized gas system, the pressurized gas system possibly comprising the relief cap interface chamber 76, the fluid transfer chamber 73, the trigger interface chamber 75, and at least a portion of the fluid chamber 127 of the hydraulic cylinder 102.

In another exemplary embodiment, if the user wanted to cease deflating the balloon dilator 202, the user may release the deflation button 62, which may cause the deflation interface 65 to cause the deflation shaft 162 and deflation ball interface 163 to move toward the deflation valve 166. This may be due at least partially to the expansion of the deflation spring 161 against the portion of the relief cap 90 surrounding the opening in the proximal end 190 and the deflation spring receiver 189. The movement of the deflation shaft 162 and the deflation ball interface 163 may also be at least partially due to the realignment of the spring-like deflation shaft positioners 162 as they act against, for example, the deflation valve legs 188. The movement of the deflation ball interface 163 away from the proximal end 190 of the relief cap 90 may cause the deflation ball 164 to become lodged against the deflation valve 166 and cover the deflation valve passage 167 so as to prevent further fluid communication through the deflation valve passage 167.

In another embodiment, there may also be a rapid depressurization valve, either on the relief cap 90, the pneumatic assembly 60, or the hydraulic assembly 100, which when triggered opens a direct and continuous flow communication channel from the pressurized gas system to the external environment.

In another embodiment, there may also be a high pressure depressurization valve 91, either on the relief cap 90, the pneumatic assembly 60, or the hydraulic assembly 100, which when triggered opens a direct and continuous flow communication channel from the pressurized gas system to the external environment. Unlike the other deflation or depressurization systems, however, the high pressure depressurization is automatic in that when the pressure in the aforementioned pressurized gas system gets to what has been predetermined as being an excessive level, the high pressure depressurization valve 91 automatically opens a direct and continuous flow communication channel from the pressurized gas system to the external environment. Once the pressure in the aforementioned pressurized gas system, however, ceases to be at the excessive level, the high pressure depressurization valve 91 may cease or close the direct flow communication from the pressurized gas system to the external environment.

For example, when the pressure in the relief cap interface chamber 76 reaches a predetermined maximum level, the fluid pressure on the poppet ball may move the poppet ball away from the interface portion. The movement of the poppet ball may compress the poppet spring, and thus the relief cap interface chamber 76 be in fluid communication with the external environment via the poppet valve 91. Once enough fluid has left the relief cap interface chamber 76 such that the pressure in the relief cap interface chamber 76 falls below, for example, the predetermined maximum level, the poppet spring may expand and relodge the poppet ball in the poppet valve 91, thus ceasing the fluid communication between the relief cap interface chamber 76 and the external environment.

This flow and/or escape of gas from the pressurized gas system, either through user initiated regular deflation or rapid depressurization, or automatic depressurization through high pressure depressurization valves, may cause the gas pressure in, for example, the aforementioned pressurized gas system to fall. This reduction in gas pressure may cause the primary piston 105 to move toward the proximal wall 122 of the hydraulic cylinder 102 in a variety of ways. For example, the reduction of gas pressure at least in the portion of the hydraulic cylinder 102 between the proximal wall 122 and proximal wall 134 of the primary piston 105 may create a vacuum, causing this vacuum to "tug" on the proximal wall 134 of the primary piston 104 and reduce the volume of the pressurized gas system. However, other forces may also be at work to reduce the pressure and/or volume of the pressurized gas system.

In another embodiment, the reduction in gas pressure in the pressurized gas system may cause the expansion piston spring 114, which is currently compressed, to expand and push the expansion piston 106 toward the proximal opening 141 in the proximal end of the hydraulic cap 104. In another embodiment, the primary piston spring 113, which is currently compressed, may expand and push the primary piston 105 toward the proximal wall 122 of the hydraulic cylinder 102. In another embodiment, this movement of the primary piston 105 toward the proximal wall 122 of the hydraulic cylinder 102 and away from the proximal end 140 of the hydraulic cap 102 may create a negative fluid pressure in the fluid system, which may comprise at least a portion of the fluid chamber 127 of the hydraulic cylinder 102, the fluid chamber 136 of the primary piston 105, at least a portion of the inner chamber 153 of the hydraulic cap 104, portions of the central portion 154 of the hydraulic cap 104, and external device to which the external device interface 101 may be connected. Accordingly, this negative fluid pressure may cause some of the fluid that had previously been ejected from the fluid delivery system 10 to reenter the device through the external device interface 101.

In an exemplary embodiment, this negative fluid pressure and/or flow of fluid back into the fluid delivery system 10 may cause the pressure sensor subassembly 116, which may be lodged in the pressure sensor port 152 of the hydraulic cap 104, to send readings to the electronic interface 104. The electronic interface 40 may receive the readings, for example, through the pressure sensor header 44 on the electronic interface feature board 54. Once receiving the readings, the electronic interface 40 may process the readings and output variations of the readings. For example, the electronic interface 40 could display on the electronic display 41 the current pressure/size readings, and the time the entire fluid delivery system 10 has been in use or otherwise. In another example, the electronic interface 40 may trigger and/or illuminate various indicators 49, 50, for example, the down indicator 49b-1, which may indicate that the pressure in the system is decreasing, and/or the pressure/size indicator lights 49a, 50, which may indicate when, for example, a balloon catheter has deflated down to various pressures/sizes.

In another exemplary embodiment, the check valve 115 may used as a fail safe component of the fluid delivery system 10. For example, in case that the pneumatic assembly 60 does not function properly and appropriate gas and/or gas pressure is not delivered to the hydraulic assembly 100, the check valve 115 could be used to introduce fluid into the hydraulic assembly 100 and facilitate the flow of fluid out of the fluid delivery system 10 via the external interface 101. For example, a needle or other similar device could be inserted into the external interface opening 179 of the valve cap 180. Then fluid could be pumped from the needle or other similar device, into the check valve 115, through the flexible interface extension 176, into the hydraulic cap interface 175, and into the hydraulic cylinder 102 via the central portion 154 of the hydraulic cap 104. As the primary piston 105 is, in its initial position, substantially flush with the proximal wall 122 of the hydraulic cylinder 102, one way the fluid chamber 127 could compensate for the fluid being inserted through the check valve 115 would be to send fluid out of the external interface 101. Accordingly, the external device, for example, a balloon dilator 200, could be filled through the use of the check valve 115.

In another embodiment, should the pneumatic assembly 60 not function properly and gas cannot be released from the pneumatic assembly 60 due to a malfunction in, for example, the relief cap 90, the check valve 115 could be used to remove fluid from the hydraulic assembly 100. In one exemplary embodiment, this could be done by placing a needle or similar device into the external interface opening 179 of the valve cap 180. Then, by drawing fluid out of the check valve 115 through the needle or other similar device, a negative fluid pressure could be created in the hydraulic assembly 100. While the movement of the primary piston 105 toward the hydraulic cap 104 may compensate for at least some of the fluid volume lost through the use of the needle, it may not be able to compensate for the entire loss, as a combination of the negative pressure that would be created by the gas present in the hydraulic cylinder 102, the resistance to compression of the primary piston spring 105, and the primary piston 105 attaining its minimum possible physical separation from the hydraulic cap 104 would prevent the movement of the primary piston 105 for compensating for all of the fluid loss. Accordingly, some of the fluid loss may have to be compensated for by drawing some fluid back into the hydraulic assembly 100 of the fluid delivery system 10 through the external interface 101.

In an exemplary embodiment, the fluid delivery system 10 may be used in conjunction with an endoscope and a balloon dilator to treat gastrointestinal strictures, or other internal diseases. The balloon dilator, which may be connected to a catheter, could be run down the working channel of an endoscope that is positioned at the desired location within a patient's gastrointestinal tract or other desired place within the patient's body. The balloon dilator may then be deployed, for example, at a desired stricture's location. The fluid delivery system 10 could then be used to fill the balloon dilator 200 to the desired size, for example, by filling the balloon dilator 200 through the external interface 101 via a catheter. Then, after holding the balloon dilator at the desired size for the desired length of time, the balloon dilator could either be increased in size, or could be deflated using the fluid delivery system 10. Once the balloon dilator was deflated, it could then be removed from the gastrointestinal tract, or other body portion, via the working channel of the endoscope.

In another exemplary embodiment, the balloon dilator may be porous, and the fluid in the fluid delivery system 10 may be a chemical. Accordingly, introducing the chemical into the porous balloon dilator could allow the porous balloon dilator to introduce the chemical at a desired location within the body. In another embodiment, the chemical may be introduced into the fluid contained within the fluid delivery system 10 through the check valve 115. In yet another embodiment, contrast may be introduced into the fluid contained within the fluid delivery system 10 through the check valve 115.

In another exemplary embodiment, the fluid delivery system 10 with the balloon dilator 200, when in use with an endoscope, may be attached to the endoscope, for example, through the use of Velcro-like fasteners or other adhesion devices, or be more permanently attached, so as to increase control and/or free up hands. Generally, the fluid delivery system 10, and any attachments, may be used in conjunction with an endoscope. For example, in a fluid delivery system 10 with the balloon dilator 200, the balloon dilator 200 may be fed down the working channel of an endoscope.

In another exemplary embodiment, a chemical may be introduced into the hydraulic assembly 100 through the check valve. 115. For example, a contrast solution, photoluminescent dye, or radioactive trace chemicals could be introduced into the fluid contained with the hydraulic assembly 100 through the check valve 115.

In yet another embodiment, the fluid delivery system 10 may use a closed feedback loop to control the fluid delivery system 10. For example, fluid delivery system 10 may have portions, for example, capacitors, configured to detect the size of the balloon. Based on that information, portions of the fluid delivery system 10, for example, the electronic interface, may automatically control balloon inflation and/or deflation rates through electronic manipulation of the hydraulic assembly 100 and/or the pneumatic assembly 60 with minimal input from the user.

In another exemplary embodiment, the fluid delivery system 10 may be configured with an automatic failsafe system. For example, should a problem arise in the system (i.e., the balloon breaks or the hydraulic assembly ruptures), the fluid delivery system 10 may be configured to detect such a failure and automatically act. In one example, the fluid delivery system 10 may shut down all of its components. In another example, the fluid delivery system 10 may be configured to automatically withdraw the balloon from its deployed location, for example, through the use of an electromechanical pulley or a similar device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A fluid delivery system for connection to a balloon catheter having a balloon, the fluid delivery system comprising:
   a first assembly including an actuator connected to a reservoir for releasing pressurized fluid from the reservoir;
   a second assembly having an inflation fluid chamber, the second assembly being connected to the first assembly to receive pressurized fluid from the first assembly and, in response to receipt of the pressurized fluid, deliver inflation fluid from the inflation fluid chamber to an external interface configured for connection to a balloon catheter; and
   an electronic interface to display information relating to a measurement of the inflation fluid in the second assembly;
   wherein the electronic interface is capable of sending a signal to the first assembly to alter inflation fluid flow at one or more predetermined measurements.

2. A fluid delivery system for connection to a balloon catheter having a balloon, the fluid delivery system comprising:
   a first assembly including an actuator connected to a reservoir for releasing pressurized fluid from the reservoir;
   a second assembly having an inflation fluid chamber, the second assembly being connected to the first assembly to receive pressurized fluid from the first assembly and, in response to receipt of the pressurized fluid, deliver inflation fluid from the inflation fluid chamber to an external interface configured for connection to a balloon catheter; and
   an electronic interface to display information relating to a measurement of the inflation fluid in the second assembly;
   wherein the electronic interface includes an indicator for emitting a signal in response to one or more states of the fluid delivery system.

3. A fluid delivery system for connection to a balloon catheter having a balloon, the fluid delivery system comprising:
   a first assembly including an actuator connected to a reservoir for releasing pressurized fluid from the reservoir;
   a second assembly having an inflation fluid chamber, the second assembly being connected to the first assembly to receive pressurized fluid from the first assembly and, in response to receipt of the pressurized fluid, deliver inflation fluid from the inflation fluid chamber to an external interface configured for connection to a balloon catheter; and
   an electronic interface to display information relating to a measurement of the inflation fluid in the second assembly;
   wherein the electronic interface is configured to store data.

4. A fluid delivery system for connection to a balloon catheter having a balloon, the fluid delivery system comprising:

a first assembly including an actuator connected to a reservoir for releasing pressurized fluid from the reservoir;

a second assembly having an inflation fluid chamber, the second assembly being connected to the first assembly to receive pressurized fluid from the first assembly and, in response to receipt of the pressurized fluid, deliver inflation fluid from the inflation fluid chamber to an external interface configured for connection to a balloon catheter;

an electronic interface to display information relating to a measurement of the inflation fluid in the second assembly; and a sensor in fluid communication with the second assembly to obtain the measurement of the inflation fluid in the second assembly;

wherein one of the sensor and the electronic interface is capable of converting the measurement into a size of a balloon.

5. A fluid delivery system for connection to a balloon catheter having a balloon, the fluid delivery system comprising:

a first assembly including an actuator connected to a reservoir for releasing pressurized fluid from the reservoir;

a second assembly having an inflation fluid chamber, the second assembly being connected to the first assembly to receive pressurized fluid from the first assembly and, in response to receipt of the pressurized fluid, deliver inflation fluid from the inflation fluid chamber to an external interface configured for connection to a balloon catheter; and an electronic interface to display information relating to a measurement of the inflation fluid in the second assembly;

wherein the electronic interface is capable of sending a signal to the first assembly to stop inflation fluid flow at a predetermined measurement.

6. The fluid delivery system of any one of claims 1, 2, 3, or 5, further comprising a sensor in fluid communication with the second assembly to obtain the measurement of the inflation fluid in the second assembly.

7. The fluid delivery system of claim 6, wherein the actuator comprises a trigger that upon actuation automatically causes the sensor to obtain the measurement of the inflation fluid and the electronic interface to display information relating to the measurement.

8. The fluid delivery system of any one of claims 1, 2, 3, 4, or 5, wherein the first assembly includes a valve connected between the actuator and the reservoir.

9. The fluid delivery system of any one of claims 1, 2, 3, 4, or 5, wherein the measurement comprises pressure.

10. The fluid delivery system of any one of claims 1, 2, 3, 4, or 5, wherein the actuator comprises a trigger that is capable upon actuation to automatically release pressurized fluid from the reservoir.

11. The fluid delivery system of any one of claims 1, 2, 3, 4, or 5, wherein the actuator is a trigger.

12. The fluid delivery system of any one of claims 1, 2, 3, 4, or 5, wherein the actuator is an electronic switch.

13. The fluid delivery system of any one of claims 1, 2, 3, 4, or 5, wherein the reservoir is a cartridge containing pressurized fluid.

14. The fluid delivery system of any one of claims 1, 2, 3, 4, or 5, wherein the information includes a measurement.

15. The fluid delivery system of any one of claims 1, 2, 3, 4, or 5, wherein the information includes whether the measurement is changing.

16. The fluid delivery system of any one of claims 1, 2, 3, 4, or 5, wherein the electronic interface includes a timer.

17. The fluid delivery system of any one of claims 1, 2, 3, 4, or 5, wherein the electronic interface includes an error indicator.

18. The fluid delivery system of any one of claims 1, 2, 3, 4, or 5, wherein the electronic interface includes a timer button.

19. The fluid delivery system of any one of claims 1, 2, 3, 4, or 5, wherein the electronic interface includes a power button.

20. The fluid delivery system of any one of claims 1, 2, 3, 4, or 5, wherein the electronic interface includes an indicator for indicating when the measurement is decreasing.

21. The fluid delivery system of any one of claims 1, 2, 3, 4, or 5, wherein the electronic interface includes an indicator for indicating when the measurement is increasing.

22. The fluid delivery system of any one of claims 1, 2, 3, 4, or 5, wherein the electronic interface includes an indicator for indicating when one or more predetermined measurements are obtained.

23. The fluid delivery system of claim 2, wherein the states include a measurement of the inflation fluid reaching a predetermined measurement.

24. The fluid delivery system of claim 2, wherein the states include a malfunction.

25. The fluid delivery system of claim 2, wherein the indicator emits an audio signal.

26. The fluid delivery system of claim 25, wherein the indicator includes a mute button.

27. The fluid delivery system of claim 3, wherein data is stored in an electronic memory.

28. The fluid delivery system of claim 3, wherein stored data includes one or more predetermined maximum inflation fluid measurements.

29. The fluid delivery system of claim 3, wherein stored data includes one or more predetermined maximum balloon sizes.

30. The fluid delivery system of any one of claims 1, 2, 3, 4, or 5, wherein the first assembly further includes a deflation actuator configured to release pressurized fluid from the first assembly.

31. The fluid delivery system of claim 30, wherein the deflation actuator is a deflation button.

32. The fluid delivery system of any one of claims 1, 2, 3, 4, or 5, wherein the first assembly further includes a deflation mechanism configured to decrease pressurized fluid pressure in the first assembly.

33. The fluid delivery system of claim 8, wherein the first assembly further includes a deflation actuator configured to release pressurized fluid from the valve.

34. The fluid delivery system of any one of claims 1, 2, 3, 4, or 5, wherein the second assembly further includes a check valve configured to inject inflation fluid into the inflation fluid chamber.

35. The fluid delivery system of claim 34, wherein the inflation fluid injected into the inflation fluid chamber is contrast.

36. The fluid delivery system of any one of claims 1, 2, 3, 4, or 5, wherein the second assembly further includes a check valve configured to remove inflation fluid from the inflation fluid chamber.

37. The fluid delivery system of claim 4, wherein the information includes the size of the balloon.

38. The fluid delivery system of claim 4, wherein the electronic interface is capable of sending a signal to the first assembly to alter inflation fluid flow at one or more predetermined sizes of the balloon.

39. The fluid delivery system of claim 4, wherein the electronic interface includes an indicator for emitting a signal in response to one or more states of the fluid delivery system.

40. The fluid delivery system of claim 39, wherein the states include the size of the balloon.

41. The fluid delivery system of claim 4, wherein the electronic interface is configured to store data.

42. The fluid delivery system of claim 41 wherein stored data includes one or more predetermined maximum balloon sizes.

43. The fluid delivery system of claim 5, wherein after the inflation fluid flow to the balloon is stopped, the electronic interface is capable of sending a signal to the first assembly to deflate the balloon.

44. The fluid delivery system of claim 5, wherein after the inflation fluid flow to the balloon is stopped, the electronic interface is capable of sending a signal to the first assembly to further inflate the balloon.

45. The fluid delivery system of claim 10, wherein the automatic release of pressurized fluid from the reservoir automatically releases pressurized fluid from the first assembly.

46. A fluid delivery system for connection to a balloon catheter having a balloon, the fluid delivery system comprising:
- a first assembly including an actuator connected to a reservoir for releasing pressurized fluid from the reservoir;
- a second assembly having an inflation fluid chamber, the second assembly being connected to the first assembly to receive pressurized fluid from the first assembly and, in response to receipt of the pressurized fluid, deliver inflation fluid from the inflation fluid chamber to an external interface configured for connection to a balloon catheter;
- an electronic interface to display information relating to a measurement of the inflation fluid in the second assembly; and
- a multiple compliance balloon connected to the balloon catheter.

* * * * *